US010435428B2

(12) United States Patent
Hudson et al.

(10) Patent No.: US 10,435,428 B2
(45) Date of Patent: Oct. 8, 2019

(54) PRODRUGS OF A JAK INHIBITOR COMPOUND FOR TREATMENT OF GASTROINTESTINAL INFLAMMATORY DISEASE

(71) Applicant: THERAVANCE BIOPHARMA R&D IP, LLC, South San Francisco, CA (US)

(72) Inventors: Ryan Hudson, San Jose, CA (US); Daniel D. Long, San Francisco, CA (US); Donna A. A. Wilton, San Francisco, CA (US); Mandy Loo, San Jose, CA (US); Patrick J. Brassil, Redwood City, CA (US)

(73) Assignee: THERAVANCE BIOPHARMA R&D IP, LLC, South San Francisco, CA (US)

( * ) Notice: Subject to any disclaimer, the term of this patent is extended or adjusted under 35 U.S.C. 154(b) by 270 days.

(21) Appl. No.: 15/358,462

(22) Filed: Nov. 22, 2016

(65) Prior Publication Data

US 2017/0145044 A1 May 25, 2017

Related U.S. Application Data

(60) Provisional application No. 62/259,273, filed on Nov. 24, 2015.

(51) Int. Cl.
*C07H 15/26* (2006.01)
*C12P 17/16* (2006.01)
*C07D 487/04* (2006.01)
*C07H 1/00* (2006.01)

(52) U.S. Cl.
CPC .......... *C07H 15/26* (2013.01); *C07D 487/04* (2013.01); *C07H 1/00* (2013.01); *C12P 17/165* (2013.01)

(58) Field of Classification Search
None
See application file for complete search history.

(56) References Cited

U.S. PATENT DOCUMENTS

| | | |
|---|---|---|
| 5,811,388 A | 9/1998 | Friend et al. |
| RE41,783 E | 9/2010 | Blumenkipf et al. |
| 2011/0086810 A1 | 4/2011 | Rodgers et al. |
| 2011/0152207 A1 | 6/2011 | Goff et al. |
| 2012/0289571 A1 | 11/2012 | Zhao et al. |
| 2014/0357557 A1* | 12/2014 | Cole ............... A61K 31/519 514/7.3 |
| 2018/0117168 A1 | 5/2018 | Cole et al. |

FOREIGN PATENT DOCUMENTS

| | | |
|---|---|---|
| CN | 106496233 A | 3/2017 |
| WO | 93/22334 A1 | 11/1993 |
| WO | 2011097087 A1 | 8/2011 |
| WO | 2017106957 A1 | 6/2017 |

OTHER PUBLICATIONS

Goracinova, K. et al., InTech, Inflammatory Bowel Disease-Advances in Pathogenesis and Management, "Drug targeting in IBD treatment-Existing and new approaches", 2012 (Year: 2012).*
Clark et al., "Discovery and Development of Janus Kinase (JAK) Inhibitors for Inflammatory Diseases", Journal of Medicinal Chemistry, 57(12):5023-5038, Jun. 26, 2014.
Jeffrey et al., "Expanded Utility of the [beta]-Glucuronide Linker: ADCs that Deliver Phenolic Cytotoxic Agents", ACS Medicinal Chemistry Letters, 1(6):277-280, Sep. 9, 2010.
International Search Report and the Written Opinion for PCT application No. PCT/US2016/063254 dated Feb. 9, 2017.
Angenault et al., "Cancer chemotherapy: A SN-38 (7-ethyl-10-hydroxycamptothecin)glucuronide prodrug for treatment by a PMT(prodrug montherapy)strategy", Bioorganic & Medicinal Chemistry Letters, 13: 947-950 (2003).
Desbene et al., "Application of the ADEPT strategy to the MDR resistance in cancer chemotherapy", Anti-cancer Drug Design, 14(2): 93-106 (1999).
Goto et al., "Synthesis and biological activity of the metabolites of diethyl 4-[(4-bromo-2-cyanophenyl)carbamoyl] benzylphosphonate (NO-1886)", Chem Pharm Bull, 44(3): 547-551 (1996).
Kiss et al., "Synthesis and O.R.D./C.D. spectra of the anomers of 2-amino-5-ethoxyphenyl d-glucopyranosiduronic acid and some derivatives thereof", Carbohydrate Research, 12: 115-129 (1970).
Kreuzer et al., "Aufbau von oligosacchariden mit glycosylfluoriden unter lewissaure-katalyse", Carbohydrate Research, 149: 347-361 (1986).
Thomas et al., "Synthesis and biological evaluation of glucuronide prodrugs of the histone deacetylase inhibitor CI-994 for application in selective cancer chemotherapy", Bioorganic & Medicinal Chemistry, 16: 8109-8116 (2008).
Papot et al., "Design of selectively activated anticancer prodrugs: Elimination and cyclization strategies", Current Medicinal Chemistry, 2(2):155-185 (2002).
Schmidt et al., "Cancer chemotherapy: A paclitaxel prodrug for ADEPT (Antibody-directed enzyme prodrug therapy)", European Journal of Organic Chemistry, pp. 2129-2134 (2001).
Schmidt et al., "In vitro fluorine-19 nuclear magnetic resonance study of the liberation of antitumor nitrogen mustard from prodrugs", Royal Society of Chemistry, J. Chem. Soc., Perkin Transactions, 1:1302-1308 (2002).
PCT International Preliminary Report and Written Opinion for PCT/US2018/033818 dated Aug. 9, 2018.
Amidon et al., "Colon-targeted oral drug delivery systems: Design trends and approaches", PharmSciTech, 16(4): 731-741, 2015.

(Continued)

*Primary Examiner* — Shaojia A Jiang
*Assistant Examiner* — Bahar Craigo
(74) *Attorney, Agent, or Firm* — Jeffrey A. Hagenah; Florence Jovic

(57) ABSTRACT

The invention provides compounds which are prodrugs of a JAK inhibitor agent for the targeted delivery of the JAK inhibitor to the gastrointestinal tract of a mammal. The invention also provides pharmaceutical compositions comprising the compounds, methods of using the compounds to treat gastrointestinal inflammatory diseases, and processes and intermediates useful for preparing the compounds.

14 Claims, 1 Drawing Sheet

(56) References Cited

OTHER PUBLICATIONS

Bouvier et al., "First enzymatically activated Taxotere prodrugs designed for ADEPT and PMT", BioOrganic & Medicinal Chemistry, 12: 969-977, 2004.

Burke et al., "Development of novel quaternary ammonium linkers for antibody-drug conjugates", Molecular Cancer Therapeutics, 15(5): 938-945, 2016.

Chourasia et al., "Pharmaceutical approaches to colon targeted drug delivery systems", J Pharm Pharmaceut Sci, 6 (1): 33-66, 2003.

Friend et al., "A colon-specific drug-delivery system based on drug glycosides and the glycosidases of colonic bacteria", J Med Chem, 27:261-266, 1984.

Friend et al., "Drug glycosides: Potential prodrugs for colon-specific drug delivery", J Med Chem, 28: 51-57, 1985.

Friend, Oral colon-specific drug-delivery, Boca Raton, FL, CRC Press, 1992.

Goff et al., "Targeted delivery of vitamin D to the colon using Beta-glucuronides of vitamin D: therapeutic effects in a murine model of inflammatory bowel disease", Am J Physiol Gastrointest Liver Physiol, 302:G460-G469, 2012.

Kagan et al., "Systems for region selective drug delivery in the gastrointestinal tract: biopharmaceutical considerations", Expert Opin. Drug Deliv., 5(6):681-692, 2008.

Kolakowski et al., "The methylene alkoxy carbamate self-immolative unit: Utilization for the targeted delivery of alcohol-containing payloads with antibody-drug conjugates", Angew. Chem. Int. Ed., 55:1-5, 2016.

Kolakowski et al., "The methylene alkoxy carbamate self-immolative unit: Utilization for the targeted delivery of alcohol-containing payloads with antibody-drug conjugates", Angew. Chem. Int. Ed., Supplement 1-59, 2016.

Lougerstay-Madec et al., "Synthesis of self-immolative glucuronide-based prodrugs of a phenol mustard", Anti-Cancer Drug Design, 13:995-1007, 1998.

Philip et al., "Colon targeted drug delivery systems: A review on primary and novel approaches", Oman Medical Journal, 25(2):70-78, 2010.

Sandborn et al., "Tofacitinib, an oral Janus Kinase inhibitor, in active ulcerative colitis", The New England Journal of Medicine, 367:616-624, 2012.

Scheline, "Drug metabolism by intestinal microorganisms", Journal of Pharmaceutical Sciences, 57(12): 2021-2037, 1968.

Schmidt et al., "Glucuronide prodrugs of hydroxy compounds for antibody directed enzyme prodrug therapy (ADEPT): A phenol nitrogen mustard carbamate", BioOrganic & Medicinal Chemistry Letters, 7(8): 1071-1076, 1997.

Tranoy-Opalinski et al., "Beta-glucuronidase-responsive prodrugs for selective cancer chemotherapy: An update", European Journal of Medicinal Chemistry, 74: 302-313, 2014.

Wolk et al., "New targeting strategies in drug therapy of inflammatory bowel disease: mechanistic approaches and oppportunities", Expert Opin. Drug Deliv., 10(9): 1275-1286, 2013.

Friend, "Colon-specific drug delivery", Advanced Drug Delivery Reviews, 7: 149-199 (1991).

Nolen et al., "Budesonide-Beta-D-glucuronide: A potential prodrug for treatment of ulcerative colitis", Journal of Pharmaceutical Sciences, 84 (6): 677-681 (Jun. 1995).

\* cited by examiner

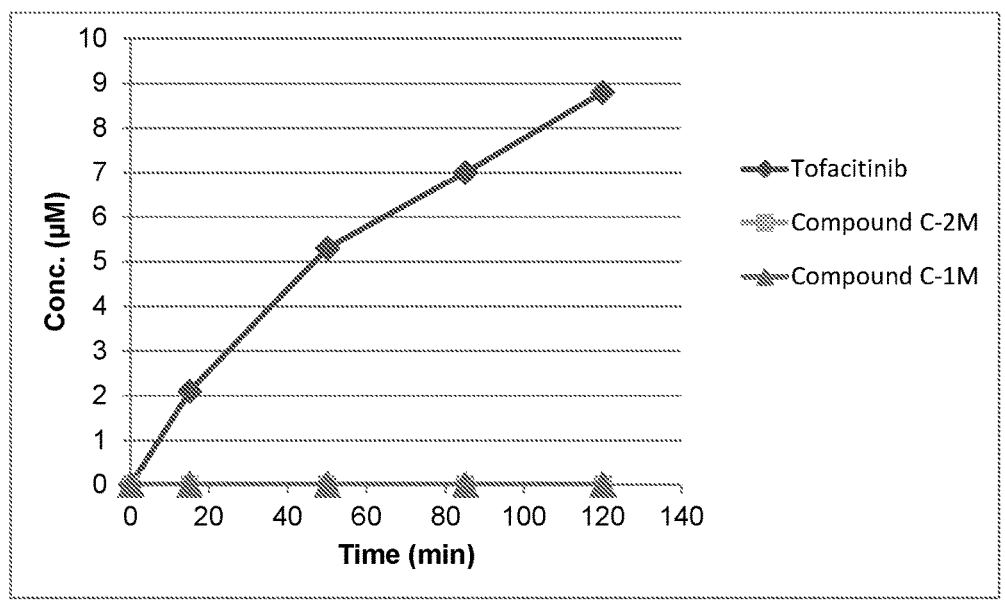

PRODRUGS OF A JAK INHIBITOR COMPOUND FOR TREATMENT OF GASTROINTESTINAL INFLAMMATORY DISEASE

CROSS-REFERENCE TO RELATED APPLICATIONS

This application claims the benefit of U.S. Provisional Application No. 62/259,273, filed on Nov. 24, 2015; the entire disclosure of which is incorporated herein by reference in its entirety.

BACKGROUND OF THE INVENTION

Field of the Invention

The invention is directed to compounds designed for targeted delivery of a JAK inhibitor to the gastrointestinal tract. The invention is also directed to pharmaceutical compositions comprising such compounds, methods of using such compounds to treat gastrointestinal inflammatory diseases, and processes and intermediates useful for preparing such compounds.

State of the Art

Inflammatory bowel disease, which primarily includes ulcerative colitis and Crohn's disease, involves chronic inflammation of all or part of the gastrointestinal tract. Ulcerative colitis is characterized by inflammation and ulceration of the mucosal layer of the rectum and the large intestine while Crohn's disease largely involves the ileum but can occur anywhere along the intestinal tract. Common symptoms include diarrhea, bloody stools, and abdominal pain. The clinical course of ulcerative colitis is intermittent, marked by alternating periods of exacerbation and remission. Incidence seems to be greater in developed than in developing countries. An estimated 1.3 million people in major industrialized countries suffer from ulcerative colitis and the numbers are expected to increase along with population growth. Patients with ulcerative colitis are at an increased risk of developing colorectal cancer. (e.g., Danese et al. *N Engl J Med*, 2011, 365, 1713-1725). In addition, an estimated 1 million people in industrialized countries suffer from Crohn's disease.

Although there exists a variety of therapeutic options to promote and maintain remission of ulcerative colitis (UC) in patients, none is ideal. Sulfasalazine-related treatments are often effective in mild UC, but much less so in moderate to severe disease. Corticosteroids are often used to provide rapid induction of remission in patients with moderate to severe UC. However, chronic use of steroids to maintain remission is discouraged due to their association with longer term adverse effects (e.g., osteoporosis and fractures, infections, cataracts, slower wound healing and suppression of adrenal gland hormone production). Systemic immunosuppressants such as azathioprine, cyclosporine and methotrexate have a slow onset and modest efficacy in moderate to severe UC patients, but prolonged use can be problematic due to consequences of long-term systemic immunosuppression (e.g., increased risk of infections and lymphoma). Anti-TNFα antibodies (e.g., infliximab and adalimumab), while expensive and requiring subcutaneous or intravenous administration, are efficacious in approximately 60 to 70% of UC patients with moderate to severe disease. However, up to one third of patients fail to respond adequately, while another third of initial responders develop tolerance over a few weeks (Allez et al., *J Crohn's Colitis*, 2010, 4, 355-366; Rutgeerts et al., *N Engl J Med*, 2005, 353, 2462-2476). The most recently approved UC therapy, vedolizumab, an anti-$\alpha_4\beta_7$ integrin antibody, is efficacious in moderate to severe UC patients although its parenteral route is suboptimal, and the consequences of long-term immunosuppression via this mechanism remain to be determined. Despite existing therapeutic options, about 10 to 20% of UC patients still require colectomy within 10 years of diagnosis (Targownik et al., *Am J Gastroenterol*, 2012, 107, 1228-1235). It is clear there remains an unmet medical need for an effective therapy to promote and maintain remission of moderate to severe UC without the safety concerns resulting from chronic, systemic immunosuppression.

While the mechanism underlying ulcerative colitis is not completely understood, it is believed that environmental factors in genetically susceptible individuals evoke an inappropriate (excessive) reaction by the immune system to gut microbiota, resulting in colonic inflammation, tissue damage, and the associated symptoms characteristic of the disease.

Although the precise pathogenesis of UC is unclear, it is apparent that proinflammatory cytokines play a pivotal role in the immunological response (Strober et al., *Gastroenterol*, 2011, 140, 1756-1767). Many of the proinflammatory cytokines most commonly elevated in UC (e.g., IL-4, IL-6, IL-13, IL-15, IL-23, IL-24, IFNγ and leptin), rely on the JAK family of tyrosine kinases (i.e., JAK1, JAK2, JAK3 and Tyk2) for signal transduction. Ligand binding to a cytokine receptor triggers autophosphorylation of its associated JAK, which in turn results in phosphorylation of a signal transducer and activator of transduction (STAT) protein. Different STATs form hetero- or homodimers and promote transcription of their target genes in the cell nucleus to regulate functions such as cell growth, differentiation and death (Clark et al., *J Med Chem*, 2014, 57, 5023-5038).

Inhibition of the family of JAK enzymes could inhibit signaling of many key proinflammatory cytokines. Thus JAK inhibitors are likely to be useful in the treatment of ulcerative colitis and other inflammatory diseases such as Crohn's disease, allergic rhinitis, asthma, and chronic obstructive pulmonary disease (COPD). However, due to the modulating effect of the JAK/STAT pathway on the immune system, systemic exposure to JAK inhibitors may have an adverse systemic immunosuppresive effect.

Tofacitinib citrate (Xeljanz®), an oral, systemically available, pan-JAK inhibitor, was approved in the United States in November, 2012 to treat adults with moderately to severely active rheumatoid arthritis who have had an inadequate response to, or who are intolerant of, methotrexate. While demonstrating superior efficacy at higher doses in clinical studies, tofacitinib was only approved at a 5 mg twice daily (BID) dose based on dose-limiting, systemically-mediated, adverse events (e.g., elevated cholesterol, increased rate of opportunistic infections, neutropenia, lymphocytopenia, lymphoma and solid tumors). The drug carries a boxed warning in the US detailing the safety risks and was declined approval in Europe based on 'significant and unresolved concerns' about the overall safety profile. Tofacitinib is under active development for UC having demonstrated a clinical response in a Phase 2 (8 week) UC trial (Sandborn et al., *N Engl J Med*, 2011, 365, 1713-1725), particularly at the 10 mg and 15 mg BID dose (See also. Panes et al., *BMC Gastroenterol*, 2015, 15, 14), doses not currently approved for any indication. The sponsor has also reported a greater proportion of patients receiving tofacitinib 10 mg BID as compared to placebo were in remission in a Phase 3 (8 week) UC induction trial and also for patients receiving tofacitinib 5 mg and 10 mg BID in a Phase 3 (52 week) UC maintenance trial.

For the treatment of ulcerative colitis and other gastrointestinal inflammatory diseases, it would be desirable to provide a compound that on oral administration achieves sufficiently high exposure of tofacitinib in the gastrointestinal tract to optimize clinical efficacy while avoiding systemic dose-limiting systemic exposure.

SUMMARY OF THE INVENTION

In one aspect, the present invention provides novel glucuronide-containing prodrugs of the JAK inhibitor tofacitinib. Such prodrugs take advantage of the gut microbiome which contains or produces an abundance of β-glucuronidase which selectively cleaves the glucuronide-containing prodrug moiety to trigger release of tofacitinib in the gastrointestinal tract, in particular in the colon.

Surprisingly, the glucuronide-containing prodrugs of the present invention are sufficiently stable to be isolated, formulated in a pharmaceutical composition and administered to a patient in need of treatment. However, they are also sufficiently labile so as to be cleaved by β-glucuronidase and further break-down to efficiently release tofacitinib. In contrast, when the glucuronide-containing prodrug moiety employed in the present invention was attached to certain other drugs known or potentially useful for treating UC, the drugs were not released on contact with β-glucuronidase (as described more fully herein below). Accordingly, the glucuronide-containing prodrugs of the present invention are particularly useful for delivering and releasing tofacitinib.

In one aspect, the present invention relates to a compound of formula (I):

(I)

[Structure of formula (I)]

wherein
n is 0, 1 or 2;
$R^1$ is selected from hydrogen, $C_{1-4}$ alkyl, $C_{1-3}$ alkoxy, amino, nitro, halo, cyano, hydroxy, and trifluromethyl;
each $R^2$, when present, is independently selected from $C_{1-4}$ alkyl, $C_{1-3}$ alkoxy, amino, nitro, halo, cyano, hydroxyl, and trifluromethyl;
$R^3$ is hydrogen, methyl or ethyl;
$R^4$ is hydrogen, methyl or ethyl;
or a pharmaceutically-acceptable salt thereof.

In another aspect, the present invention relates to a compound of formula (II):

(II)

[Structure of formula (II)]

wherein
$R^1$ is selected from hydrogen, $C_{1-4}$ alkyl, $C_{1-3}$ alkoxy, amino, nitro, halo, cyano, hydroxy, and trifluoromethyl;
or a pharmaceutically-acceptable salt thereof.

In one embodiment, the invention provides a compound of formula (II) wherein $R^1$ is selected from hydrogen, methyl, methoxy, amino, nitro, and chloro, or a pharmaceutically-acceptable salt thereof.

In another aspect, the present invention relates to a compound of formula 1:

I

[Structure of formula I]

or a pharmaceutically acceptable salt thereof.

The compound of formula 1 has demonstrated low oral bioavailability and robust release of tofacitinib (2)

2

[Structure of formula 2]

in vivo upon oral administration in preclinical species resulting in a marked increase in the ratio of colon exposure to plasma exposure relative to that obtained on oral dosing of tofacitinib itself.

In one embodiment, the compound of formula 1 produces tofacitinib or a salt thereof, upon contact with β-glucuronidase.

In another aspect, the present invention relates to a pharmaceutical composition comprising a pharmaceutically acceptable-carrier and a compound of formula (I), (II) or 1, or a pharmaceutically acceptable salt thereof; or any specific embodiments thereof described herein.

In another aspect, the present invention relates to a method of treating a gastrointestinal inflammatory disease in a mammal, the method comprising administering to the mammal a pharmaceutical composition comprising a pharmaceutically acceptable-carrier and a compound of formula (I), (II) or 1, or a pharmaceutically acceptable salt thereof; or any specific embodiments thereof described herein.

In one embodiment, the gastrointestinal inflammatory disease is ulcerative colitis. In another embodiment, the gastrointestinal inflammatory disease is Crohn's disease. And in another embodiment, the gastrointestinal inflammatory disease is colitis associated with immune checkpoint inhibitor therapy.

In another aspect, the present invention relates to a method of delivering tofacitinib to the gastrointestinal tract of a mammal, in particular, to the colon, the method comprising orally administering to the mammal a glucuronide-containing prodrug of tofacitinib which prodrug is cleaved by β-glucuronidase in the gastrointestinal tract to release tofacitinib.

In separate and distinct embodiments, the glucuronide-containing prodrug of tofacitinib is a compound of formula (I), (II) or 1, or a pharmaceutically acceptable salt thereof; or any specific embodiments thereof described herein.

In another aspect, the present invention relates to a process for preparing a compound of formula (I) or a pharmaceutically acceptable salt thereof, the process comprising deprotecting a compound of formula (I-A):

(I-A)

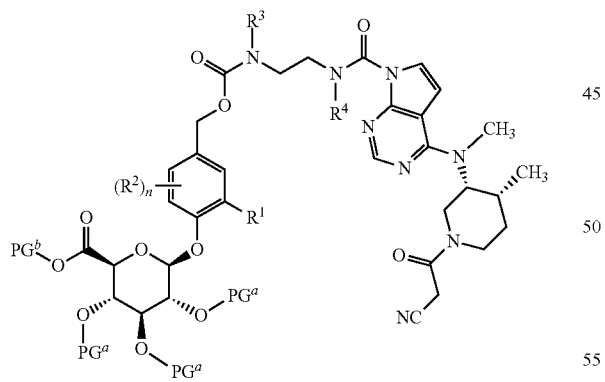

or a salt thereof; wherein $R^1$, $R^2$, $R^3$, $R^4$ and n are as defined herein; each $PG^a$ is independently a hydroxyl protecting group; and $PG^b$ is a carboxyl protecting group; to provide a compound of formula (I) or a pharmaceutically acceptable salt thereof.

In one embodiment of this process, $R^1$ is nitro; $R^3$ and $R^4$ are methyl; each $PG^a$ is acetyl; $PG^b$ is methyl; and n is 0.

In another aspect, the present invention relates to a compound of formula (I-A), or a salt thereof; or any specific embodiments thereof described herein.

In another aspect, the present invention relates to a process for preparing a compound of formula 1, or a pharmaceutically acceptable salt thereof, the process comprising:

(a) reacting a compound of formula 12'

12'

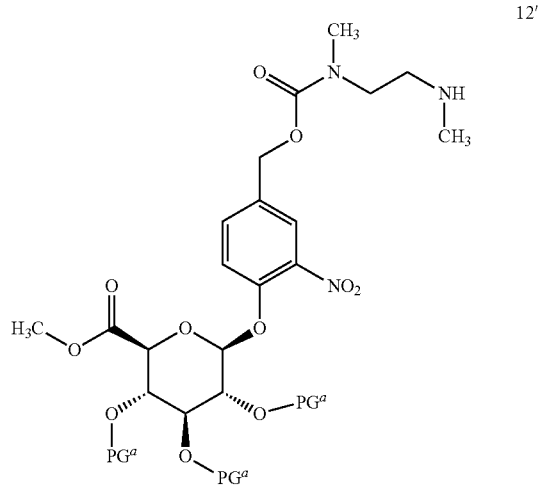

or a salt thereof; wherein each $PG^a$ is independently a hydroxyl protecting group, with a compound of formula 13

13

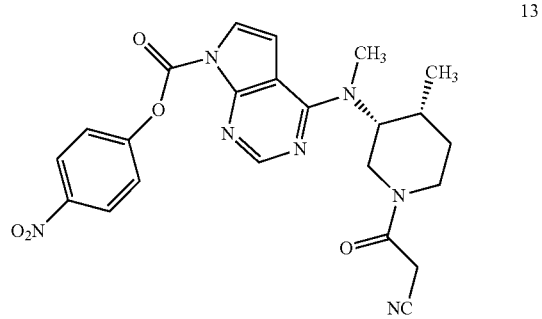 [SMILES: C[C@@H]1CCN(C(=O)CC#N)C[C@@H]1N(C)c1ncnc2c1ccn2C(=O)Oc1ccc([N+](=O)[O-])cc1]

to provide a compound of formula 14':

14'

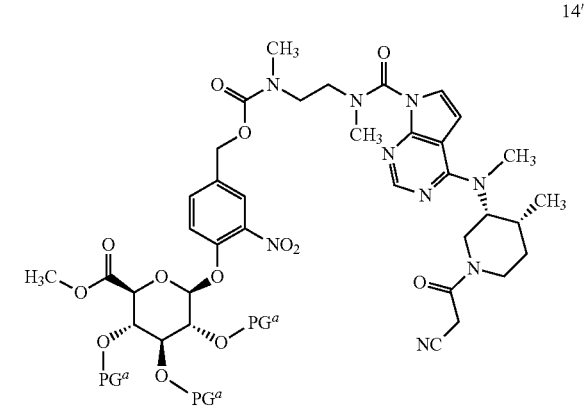

and (b) deprotecting the compound of formula 14' to provide the compound of formula 1 or a pharmaceutically acceptable salt thereof.

In one embodiment of this process, $PG^a$ is acetyl.

In separate and distinct aspects, the present invention also relates to a compound of formula 13, or a salt thereof; and a compound of formula 14' or a salt thereof, or any specific embodiments thereof described herein.

In separate and distinct aspects, the present invention also relates to other synthetic processes and intermediates described herein, which are useful for preparing the compounds of the invention.

In separate and distinct aspects, the present invention also relates to a compound of formula (I), (II) or 1, or a pharmaceutically acceptable salt thereof; or any specific embodiments thereof described herein; for use in medical therapy; or for use in the manufacture of a medicament or a formulation. In one embodiment, the medicament or formulation is for treating a gastrointestinal inflammatory disease in a mammal.

Other aspects and embodiments of this invention are disclosed herein.

BRIEF DESCRIPTION OF THE DRAWING

FIG. 1 illustrates the concentration of active metabolites, tofacitinib and compounds C-1M and C-2M, respectively as a function of time as a result of incubation of the compound of the invention (compound 1) and of comparison compounds C-1 and C-2 with rat colon content.

DETAILED DESCRIPTION OF THE INVENTION

Among other aspects, the invention provides glucuronide prodrugs of the JAK kinase inhibitor tofacitinib, pharmaceutically-acceptable salts thereof, and intermediates for the preparation thereof.

Chemical structures are named herein according to IUPAC conventions as implemented in ChemDraw software (PerkinElmer, Inc., Cambridge, Mass.). According to the convention, the compound of formula 1 may be identified as: (2S,3S,4S,5R,6S)-6-(4-((((2-(4-(((3R,4R)-1-(2-cyano-acetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)-2-nitrophenoxy)-3,4,5-trihydroxytetrahydro-2H-pyran-2-carboxylic acid, while tofacitinib (2) may be identified as 3-((3R,4R)-4-methyl-3-(methyl(7H-pyrrolo[2,3-d]pyrimidin-4-yl)amino)piperidin-1-yl)-3-oxopropanenitrile.

The compounds of the invention contains multiple chiral centers. The depiction or naming of a particular stereoisomer means the indicated stereocenter has the designated stereochemistry with the understanding that minor amounts of other stereoisomers may also be present unless otherwise indicated, provided that the utility of the depicted or named compound is not eliminated by the presence of another stereoisomer.

Definitions

When describing this invention including its various aspects and embodiments, the following terms have the following meanings, unless otherwise indicated.

The singular terms "a," "an" and "the" include the corresponding plural terms unless the context of use clearly dictates otherwise.

The term "alkyl" means a monovalent saturated hydrocarbon group which may be linear or branched or combinations thereof. Unless otherwise defined, such alkyl groups typically contain from 1 to about 10 carbon atoms. Representative alkyl groups include, by way of example, methyl, ethyl, n-propyl, isopropyl, n-butyl, sec-butyl, isobutyl, tert-butyl, n-pentyl, n-hexyl, 2,2-dimethylpropyl, 2-methylbutyl, 3-methylbutyl, 2-ethylbutyl, 2,2-dimethylpentyl, 2-propylpentyl, and the like.

When a specific number of carbon atoms are intended for a particular term, the number of carbon atoms is shown preceding the term. For example, the term "$C_{1-3}$ alkyl" means an alkyl group having from 1 to 3 carbon atoms wherein the carbon atoms are in any chemically-acceptable configuration, including linear or branched configurations.

The term "alkoxy" means the monovalent group —O-alkyl, where alkyl is defined as above. Representative alkoxy groups include, by way of example, methoxy, ethoxy, propoxy, butoxy, and the like.

The term "halo" means fluoro, chloro, bromo or iodo.

The term "therapeutically effective amount" means an amount sufficient to effect treatment when administered to a patient in need of treatment.

The term "treatment" as used herein means the treatment of a disease, disorder, or medical condition (such as a gastrointestinal inflammatory disease), in a patient, such as a mammal (particularly a human) which includes one or more of the following:

(a) preventing the disease, disorder, or medical condition from occurring, i.e., preventing the reoccurrence of the disease or medical condition or prophylactic treatment of a patient that is pre-disposed to the disease or medical condition;

(b) ameliorating the disease, disorder, or medical condition, i.e., eliminating or causing regression of the disease, disorder, or medical condition in a patient, including counteracting the effects of other therapeutic agents;

(c) suppressing the disease, disorder, or medical condition, i.e., slowing or arresting the development of the disease, disorder, or medical condition in a patient; or (d) alleviating the symptoms of the disease, disorder, or medical condition in a patient.

The term "pharmaceutically acceptable salt" means a salt that is acceptable for administration to a patient or a mammal, such as a human (e.g., salts having acceptable mammalian safety for a given dosage regime). Representative pharmaceutically acceptable salts derived from acids include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

Salts derived from pharmaceutically-acceptable inorganic bases include ammonium, calcium, magnesium, potassium, sodium, and zinc, and the like. Salts derived from pharmaceutically-acceptable organic bases include salts of arginine, choline, glucamine, lysine, benethamine, benzathine, betaine, 2-dimethylaminoethanol, 2-diethylaminoethanol, hydrabamine, morpholine, tromethamine, diethanolamine, ethanolamine, ethylenediamine, triethanolamine, 1H-imidazole, piperazine, and the like.

The term "salt thereof", as used herein, means an ionic compound in which a form of a compound of formula (I) is either the anion or cation of the ionic compound. For example, the anion of the ionic compound can be a carboxylate anion that is a deprotonated form of a compound of formula (I). The cation can be a protonated form of a compound of formula (I), i.e. a form where an amino group has been protonated by an acid. Typically, the salt is a pharmaceutically acceptable salt, although this is not required for salts of intermediate compounds that are not intended for administration to a patient.

Neutral compounds of formula (I) may optionally take the form of a zwitterion, where the term "zwitterion" means a neutral molecule with both positive and negative electrical charges.

The term "hydroxyl-protecting group" means a protecting group suitable for preventing undesired reactions at a hydroxyl group. Representative hydroxyl-protecting groups include, but are not limited to, alkyl groups, such as methyl, ethyl, and tert-butyl; allyl groups; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

The term "carboxyl-protecting group" means a protecting group suitable for preventing undesired reactions at a carboxyl group. Representative carboxyl-protecting groups include, but are not limited to, alkyl groups, such as methyl, ethyl, tert-butyl, and the like; arylmethyl groups, such as benzyl, 4-nitrobenzyl, 4-methoxybenzyl and the like; thiol groups, such as —S-tert-butyl and the like; silyl groups, such as trimethylsilyl, tert-butyldimethylsilyl and the like; oxazolines; and the like.

All other terms used herein are intended to have their ordinary meaning as understood by persons having ordinary skill in the art to which they pertain.

Representative Embodiments and Subgeneric Groupings

The following substituents and values are intended to provide representative examples of various aspects and embodiments of this invention. These representative values are intended to further define and illustrate such aspects and embodiments and are not intended to exclude other embodiments or to limit the scope of this invention.

In one embodiment, $R^1$ is hydrogen, $C_{1-4}$ alkyl, $C_{1-3}$ alkoxy, amino, nitro, halo, cyano, hydroxy, or trifluoromethyl. In another embodiment, $R^1$ is hydrogen, $C_{1-4}$ alkyl, $C_{1-3}$ alkoxy, amino, nitro, or chloro. In another embodiment, $R^1$ is hydrogen, methyl, methoxy, amino, nitro or chloro. In a particular embodiment, $R^1$ is hydrogen. In another particular embodiment, $R^1$ is nitro.

In one embodiment, n is 0. In another embodiment, n is 1. In another embodiment, n is 2.

When n is 1, in one embodiment, $R^2$ is $C_{1-4}$ alkyl, $C_{1-3}$ alkoxy, amino, nitro, halo, cyano, hydroxyl, or trifluromethyl. In another embodiment, $R^2$ is $C_{1-4}$ alkyl, $C_{1-3}$ alkoxy, amino, nitro, fluoro or chloro. In another embodiment, $R^2$ is methyl, methoxy, amino, nitro, fluoro or chloro. In a particular embodiment, $R^2$ is fluoro.

When n is 1, the $R^2$ substituent may be in any available position of the phenyl ring to which $R^2$ is attached. In one embodiment, $R^2$ is ortho to $R^1$. In another embodiment, $R^2$ is meta to $R^1$. In another embodiment, $R^2$ is para to $R^1$.

When n is 2, in one embodiment, each $R^2$ is independently $C_{1-4}$ alkyl, $C_{1-3}$ alkoxy, amino, nitro, halo, cyano, hydroxyl, or trifluromethyl. In another embodiment, each $R^2$ is independently $C_{1-4}$ alkyl, $C_{1-3}$ alkoxy, amino, nitro, fluoro or chloro. In another embodiment, each $R^2$ is independently methyl, methoxy, amino, nitro, fluoro or chloro. In a particular embodiment, each $R^2$ is fluoro.

When n is 2, the $R^2$ substituents may be in any available position of the phenyl ring to which $R^2$ is attached. In one embodiment, the $R^2$ substituents are ortho and meta to $R^1$. In another embodiment, the $R^2$ substituents are ortho and para to $R^1$. In another embodiment, the $R^2$ substituents are meta and para to $R^1$.

In one embodiment, $R^3$ is hydrogen. In another embodiment, $R^3$ is methyl. In another embodiment, $R^3$ is ethyl.

In one embodiment, $R^4$ is hydrogen. In another embodiment, $R^4$ is methyl. In another embodiment, $R^4$ is ethyl.

In one embodiment, both $R^3$ and $R^4$ are methyl. In another embodiment, one of $R^3$ and $R^4$ is hydrogen and the other is methyl.

In one embodiment, n is 0; $R^1$ is hydrogen, methyl, methoxy, amino, nitro or chloro; $R^3$ is methyl; and $R^4$ is methyl.

In another embodiment, n is 0; $R^1$ is hydrogen, methyl, methoxy, amino, nitro or chloro; $R^3$ is hydrogen; and $R^4$ is methyl.

In another embodiment, n is 0; $R^1$ is hydrogen, methyl, methoxy, amino, nitro or chloro; $R^3$ is methyl; and $R^4$ is hydrogen.

In another embodiment, n is 0; $R^1$ is hydrogen, methyl, methoxy, amino, nitro or chloro; $R^3$ is ethyl; and $R^4$ is ethyl.

In another embodiment, n is 1; $R^1$ is hydrogen, methyl, methoxy, amino, nitro or chloro; $R^2$ is methyl, methoxy, amino, nitro, fluoro or chloro; $R^3$ is methyl; and $R^4$ is methyl.

In another embodiment, n is 1; $R^1$ is hydrogen, methyl, methoxy, amino, nitro or chloro; $R^2$ is methyl, methoxy, amino, nitro, fluoro or chloro; $R^3$ is hydrogen; and $R^4$ is methyl.

In another embodiment, n is 1; $R^1$ is hydrogen, methyl, methoxy, amino, nitro or chloro; $R^2$ is methyl, methoxy, amino, nitro, fluoro or chloro; $R^3$ is methyl; and $R^4$ is hydrogen.

Synthetic Procedures

Compounds of formula (I) may be prepared according to the synthetic approach described in detail in the appended examples. As illustrated in Scheme 1 specifically for the preparation of the compound of formula 1, the key step of the synthesis is the formation of the urea linkage between tofacitinib and a protected form of the glucuronide prodrug moiety 12'. In Scheme 1, $PG^a$ represents a hydroxyl protecting group, preferably allyl or acetyl, although other hydroxyl protecting group may also be used including a silyl protecting group such as tert-butyldimethylsilyl.

Scheme 1

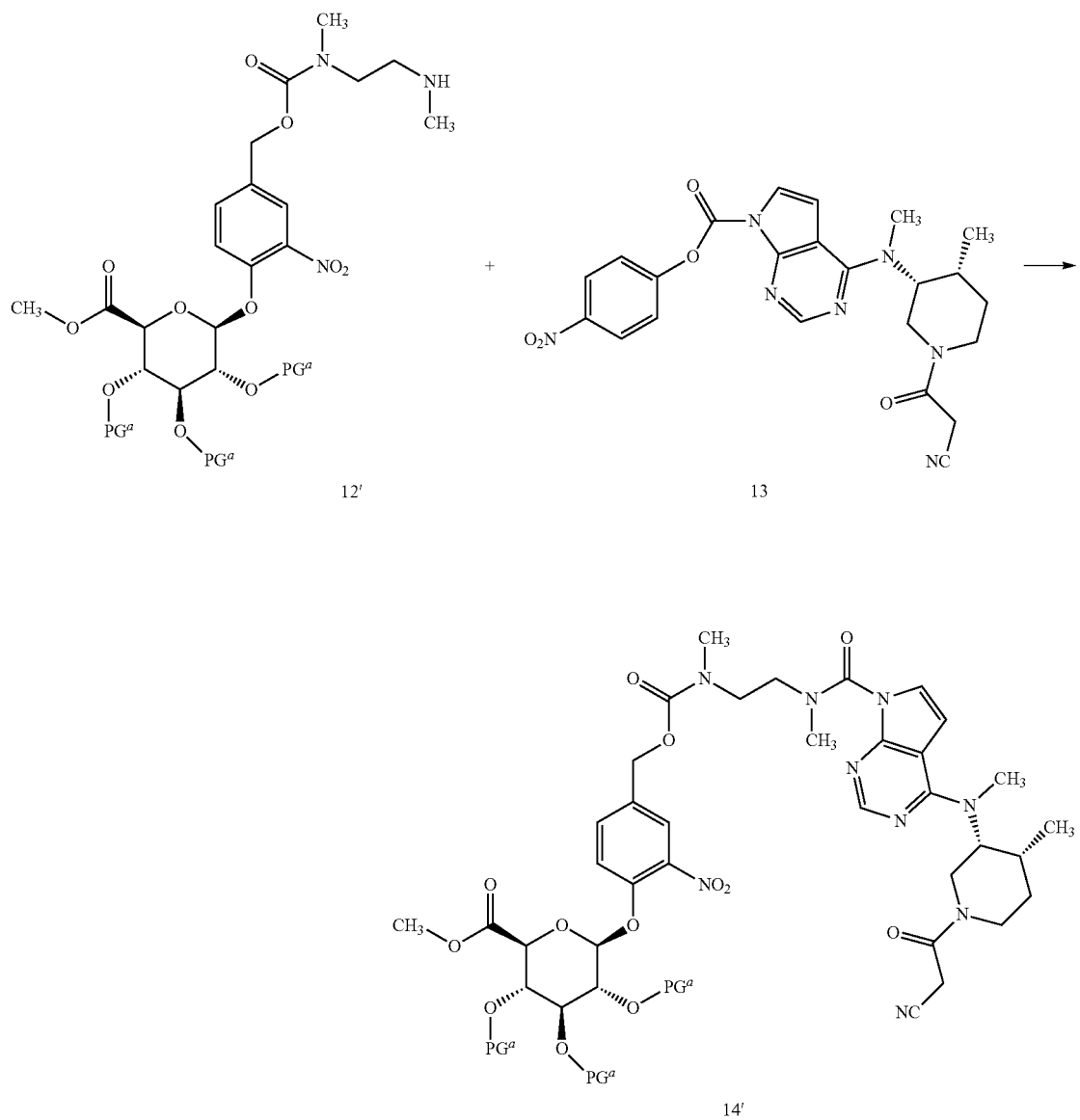

Formation of this key urea linkage initially focused on using tofacitinib as the nucleophile; however this bond forming step was found to be inconsistent as reaction of tofacitinib with a range of different electrophiles only led to formation of the desired product in low yields. It was therefore deemed necessary to switch the role of the two partners and make a tofacitinib derivative the electrophilic reacting partner, and the glucuronide prodrug moiety the nucleophile. After surveying many reagents, it was determined that tofacitinib could be derivatized and rendered electrophilic when it was joined to a reactive para-nitrophenyl or pentafluorophenyl moiety via a carbamate linkage. For example, para-nitrophenyl chloroformate, bis(4-nitrophenyl) carbonate, or bis(pentafluorophenyl) carbonate reagents were able to achieve the desired balance of being reactive enough to affect the bond formation with tofacitinib, while also providing an intermediate which was not so reactive that it decomposes before reaction with the glucuronide species. The resulting protected intermediate 14' is deprotected, for example when $PG^a$ is an acetate group, with lithium hydroxide in a subsequent step to provide the compound of formula 1.

Accordingly, in one aspect, the invention provides a process of preparing compound 1, the process comprising (a) reacting a protected glucuronide prodrug moiety 12' with an electrophilic tofacitinib derivative 13 to provide compound 14', and (b) deprotecting compound 14' to provide the compound of formula 1. In a further aspect, the invention provides the electrophilic tofacitinib compound 13.

The action of a β-glucuronidase enzyme on the prodrugs of the invention is illustrated for the compound of formula 1. As shown in Scheme 2, upon action of a β-glucuronidase enzyme on the compound of formula 1, tofacitinib is released by a multistep process:

Scheme 2

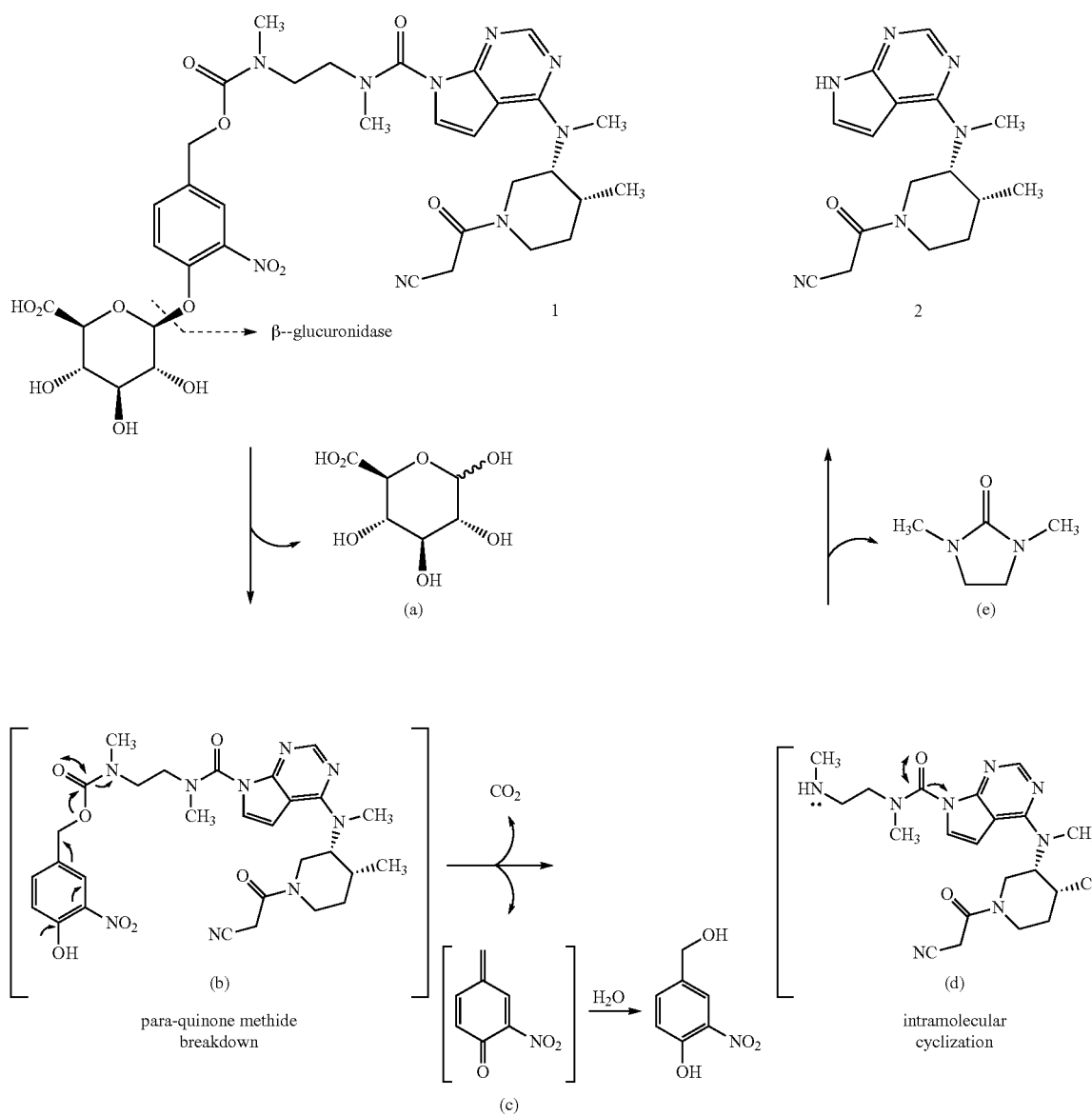

In the initial step, the β-glucuronidase enzyme cleaves the glycosidic bond of the compound of formula 1, causing glucuronic acid (a) to be released and the formation of an aglycone intermediate (b). The aglycone spontaneously decomposes to afford a quinone methide species (c) which can be trapped with water, and a transient carbamic acid which loses carbon dioxide to afford a diamine (d). Intramolecular cyclization of the diamine leads to the formation of an imidazolidinone derivative (e) and release of tofacitinib.

As described in the experimental section below, the conversion of the compound of formula 1 to tofacitinib via the intermediate steps illustrated in Scheme 2 has been observed in incubations with purified β-glucuronidase (Assay 2) and with freshly prepared rat colon content homogenate (Assay 3). In these latter experiments, the concentrations of the compound of formula 1, the aglycone intermediate b, the diamine intermediate d, and tofacitinib were monitored as a function of time. The rapid disappearance of the compound of formula 1 was accompanied by the rapid and transient formation of the aglycone b and the slower, rate-determining appearance of the diamine d and the ultimate active metabolite tofacitinib.

The present investigators have determined that the multistep decomposition of the glucuronide prodrug compound starting with the bacterial β-glucuronidase enzymatic cleavage of the glycosidic bond to beneficially deliver a desired active moiety directly to the site of action in the colon depends sensitively on the nature of the linkage and on the specific active moiety. Mesalamine, 5-aminosalicylic acid (5-ASA) (compound C-1M) is an older agent, long used for the treatment of mild to moderate ulcerative colitis. However, the present glucuronide prodrug approach does not appear to be applicable for delivering 5-ASA directly to the colon. The glucuronide prodrug of 5-ASA (compound C-1)

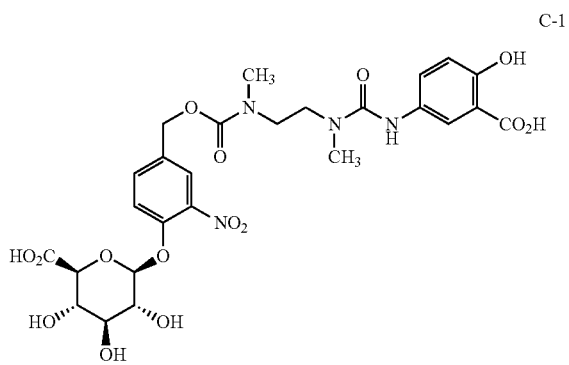

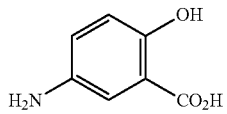

was incubated with rat colon content homogenate in an analogous experiment to that noted above. While a transient aglycone analogous to aglycone b in Scheme 2 and a slower appearance of a diamine analogous to d were observed on a time scale similar to that for the compound of formula 1, no evidence of active metabolite 5-ASA could be found.

A recent publication US2013/0109720 disclosed 2-(5-fluoro-4-methylpyridin-3-yl)-5-(4-methyl-6-(methylsulfonyl)pyridin-3-yl)-1H-indole (compound C-2M) as a calcium release-activated calcium channel (CRAC) inhibitor. CRAC inhibitors are also believed to be useful for the treatment of inflammatory diseases. However, the present glucuronide prodrug approach also does not appear to be applicable for the targeted delivery of this CRAC inhibitor. The breakdown of the CRAC inhibitor prodrug C-2

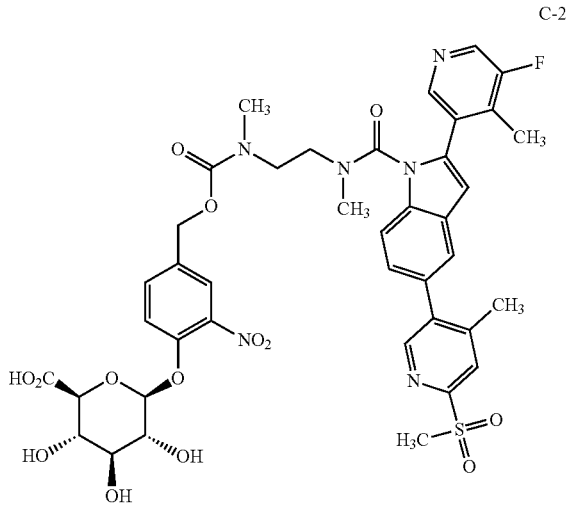

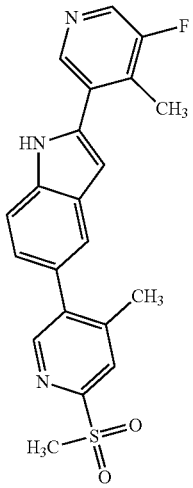

was also studied in rat colon content homogenate with results similar to those obtained for compound C-1. While intermediate breakdown products were observed, no evidence of release of the active CRAC inhibitor C-2M could be found.

The present evidence suggests the prodrugs of the invention are uniquely suited to take advantage of a bacterial β-glucuronidase-initiated breakdown mechanism to release tofacitinib in the colon.

Pharmaceutical Compositions

The compounds of the invention and pharmaceutically-acceptable salts thereof are typically used in the form of a pharmaceutical composition or formulation. Accordingly, in one of its compositions aspects, the invention is directed to a pharmaceutical composition comprising a pharmaceutically-acceptable carrier or excipient and a compound of formula (I), (II), or 1, or a pharmaceutically-acceptable salt thereof. Optionally, such pharmaceutical compositions may contain other therapeutic and/or formulating agents if desired.

The pharmaceutical compositions of the invention typically contain a therapeutically effective amount of a compound of the present invention. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.1 to about 95% by weight of the compound of formula (I); including from about 5 to about 70% by weight; such as from about 10 to about 60% by weight of the compound of formula (I).

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending a compound of the invention with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of the present compounds calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise a compound of the invention and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, dicalcium phosphate, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as crosscarmellose sodium, agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid, methacrylic acid ester copolymers, cellulose acetate trimellitate, carboxymethyl ethyl cellulose, hydroxypropyl methyl cellulose acetate succinate, and the like.

Pharmaceutical compositions of the invention may also be formulated to provide slow or controlled release of the active agent using, by way of example, hydroxypropyl methyl cellulose in varying proportions; or other polymer matrices, liposomes and/or microspheres. In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), oleic acid, glycerol, tetrahydrofuryl alcohol, polyethylene glycols and fatty acid esters of sorbitan, and mixtures thereof. Alternatively, certain liquid formulations can be converted, for example, by spray drying, to a powder, which is used to prepare solid dosage forms by conventional procedures.

Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The following non-limiting examples illustrate representative pharmaceutical compositions of the present invention.

Tablet Oral Solid Dosage Form

A compound of the invention or a pharmaceutically-acceptable salt thereof is dry blended with microcrystalline cellulose, polyvinyl pyrrolidone, and croscarmellose sodium in a ratio of 4:5:1:1 and compressed into tablets to provide a unit dosage of, for example, 4 mg, 10 mg or 20 mg active agent per tablet.

Tablet Oral Solid Dosage Form

A compound of the invention or a pharmaceutically-acceptable salt thereof (40 g) is thoroughly blended with microcrystalline cellulose (445 g), silicon dioxide fumed (10 g), and stearic acid (5 g). The mixture is then compressed on a tablet press to form tablets weighing 100 mg each. Each tablet provides 8 mg of the active agent per unit dose suitable for oral administration.

Tablet Oral Solid Dosage Form

A compound of the invention or a pharmaceutically-acceptable salt thereof (10 g) is thoroughly blended with cornstarch (50 g), croscarmellose sodium (25 g), lactose (110 mg), and magnesium stearate (5 mg). The mixture is then compressed on a tablet press to form tablets weighting 200 mg each. Each tablet provides 10 mg of the active agent per unit dose suitable for oral administration.

Capsule Oral Solid Dosage Form

A compound of the invention or a pharmaceutically-acceptable salt thereof is combined with microcrystalline cellulose, polyvinyl pyrrolidone, and crosscarmellose sodium in a ratio of 4:5:1:1 by wet granulation and loaded into gelatin or hydroxypropyl methylcellulose capsules to provide a unit dosage of, for example, 4 mg, 10 mg or 20 mg active agent per capsule.

Powder in Capsules

A compound of the invention or a pharmaceutically-acceptable salt thereof (1 to 50 mg) is filled into an empty hydroxypropyl methylcellulose (HPMC) capsule intended for oral administration.

Liquid Formulation

A compound of the invention or a pharmaceutically-acceptable salt thereof (50 mg) is mixed with and fully dissolved in 100 mL low calorie mixed berry sport drink in a capped bottle. Various volumes of this solution are measured out to provide different dose levels.

Liquid Formulation

A liquid formulation comprising a compound of the invention (0.1%), water (98.9%) and ascorbic acid (1.0%) is formed by adding a compound of the invention to a mixture of water and ascorbic acid.

Enteric Coated Oral Dosage Form

A compound of the invention is dissolved in an aqueous solution containing polyvinyl pyrrolidone and spray coated onto microcrystalline cellulose or sugar beads in a ratio of 1:5 w/w active agent:beads and then an approximately 5% weight gain of an enteric coating comprising an acrylic copolymer, for example a combination of acrylic copolymers available under the tradenames Eudragit-L® and Eudragit-S®, or hydroxypropyl methylcellulose acetate succinate is applied. The enteric coated beads are loaded into gelatin or hydroxypropyl methylcellulose capsules to provide a unit dosage of, for example, 5 mg active agent per capsule.

Enteric Coated Oral Dosage Form

An enteric coating comprising a combination of Eudragit-L® and Eudragit-S®, or hydroxypropyl methylcellulose acetate succinate is applied to a tablet oral dosage form or a capsule oral dosage form described above.

Utility

The present compounds have been designed to deliver a clinically efficacious agent directly to the site of action in gastrointestinal tract for the treatment of gastrointestinal inflammatory diseases, in particular for the treatment of inflammatory bowel diseases such as ulcerative colitis and Crohn's disease. The compounds are also expected to be useful for the treatment of colitis associated with immune checkpoint inhibitor therapies. In particular, the glucuronide prodrugs of the invention are designed to take advantage of the abundance of bacterial β-glucuronide enzyme in the gastrointestinal tract, in particular in the colon, to release the JAK inhibitor tofacitinib predominantly in the lower gastrointestinal tract. Further, exemplary compounds of the invention have been shown to be poorly systemically absorbed, thus minimizing the risk of immunosuppression.

The present prodrug compounds are designed to lack biological activity. For example, the compound of formula 1 has no significant affinity for, or potency at, the Janus kinase (JAK) family of enzymes, non-JAK enzymes, or a range of G-protein coupled receptors, ion channels and transporters which may be expressed in the gastrointestinal (GI) tract or systemically. Biological activity following administration of the present compounds is attributable to generated tofacitinib.

As described in the experimental section below, the present compounds have been extensively profiled in one or more preclinical assays. Compounds have been shown to decompose in the presence of the β-glucuronidase present in rat colon feces. For example, the metabolic stability of the compound of formula 1 and the formation of tofacitinib were investigated in homogenate incubations of intestinal lumen content isolated from the duodenum, ileum, jejunum and colon of rat. The compound exhibited a gradient of increasing turnover from stable in duodenum and jejunum content (half-life>60 minutes) to modest turnover in ileum content (half-life 34 minutes) to rapid turnover in the colon content (half-life<5 minutes) with evidence of tofacitinib formation. The gradient of increasing compound turnover reflects the increasing presence of bacteria from upper GI to lower GI.

The release of tofacitinib from the present compounds upon oral dosing has been studied in mouse, rat, and cynomolgus monkeys. As described in Assays 4, 5, 9, and 10, below, in all species, the prodrugs exhibited a significantly higher exposure of tofacitinib in the colon than exposure in plasma. In particular, the release of tofacitinib from the compound of formula 1 in specific segments of the gastrointestinal tract was studied in rat and monkey and compared with the concentration obtained from oral dosing of tofacitinib itself at equivalent doses. Not only did compound 1 exhibit a significantly higher exposure throughout the gastrointestinal tract than exposure in plasma (for example, ratios greater than 500 in rat and between about 60 and 150 in monkey in colon segments) but also showed an increase in the GI tissue concentration and in the GI tissue to plasma concentration ratio relative to that obtained from oral dosing of tofacitinib itself. For example, in monkey, a five- to seven-fold increase in tofacitinib concentration in cecum, proximal, and distal colon tissue was observed from oral administration of the prodrug as compared with that obtained from oral tofacitinib.

Efficacy of certain compounds of the invention was also tested in the oxazolone-induced colitis model in mice. The compounds of formula 1 and 4 demonstrated activity in the oxazolone-induced colitis model in mice at lower oral doses than required by direct administration of tofacitinib to achieve an equivalent effect. In addition, the efficacious doses of the compound of formula 1 are associated with reduced systemic exposure of tofacitinib relative to the systemic exposure obtained from dosing tofacitinib itself at its efficacious dose. In a model of immunosuppression in mice, compound 1 demonstrated minimal effect of immunosuppression at the same dose required to demonstrate comparable efficacy in the oxazolone model (therapeutic index>3-fold) whereas tofacitinib is immunosuppressive at a dose lower than its efficacious dose (therapeutic index≤0.3).

Accordingly, the glucuronide prodrugs of tofacitinib of the invention are expected to be useful for the treatment of inflammatory bowel disease, in particular ulcerative colitis. The present compounds are also expected to be useful for the treatment of Crohn's disease and for the treatment of colitis associated with immune checkpoint inhibitor therapy, a potentially serious consequence of cancer immunotherapies. Immune checkpoint inhibitor therapies include, but are not limited to, cytotoxic T lymphocyte associated antigen 4 (CTLA-4) inhibitors, such as ipilimumab (Yervoy®) and tremelimumab; programmed cell death 1 (PD-1) inhibitors, such as pembrolizumab (Keytruda®) and nivolumab (Opdivo®); and programmed death ligand 1 (PD-L1) inhibitors, such as atezolizumab (Tecentriq®), durvalumab, and avelumab. In particular, the compounds are expected to be useful for the treatment of CTLA-4 inhibitor-induced colitis. The compounds may also find utility in the treatment of additional conditions such as the gastrointestinal adverse effects in graft versus host disease, celiac sprue, microscopic colitis, pouchitis, and autoimmune enteropathy.

In one aspect, therefore, the invention provides a method of treating a gastrointestinal inflammatory disease in a mammal (e.g., a human), the method comprising administering to the mammal a therapeutically-effective amount of a compound of the invention or of a pharmaceutical composition comprising a pharmaceutically-acceptable carrier and the compound of the invention.

In one embodiment, the gastrointestinal inflammatory disease is ulcerative colitis. In another embodiment, the gastrointestinal inflammatory disease is Crohn's disease. And in another embodiment, the gastrointestinal inflammatory disease is colitis associated with immune checkpoint inhibitor therapy.

The invention further provides a method of treating ulcerative colitis in a mammal, the method comprising administering to the mammal a therapeutically-effective amount of a compound of the invention or of a pharmaceutical composition comprising a pharmaceutically-acceptable carrier and a compound of the invention.

When used to treat ulcerative colitis, the compound of the invention will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating ulcerative colitis and other gastrointestinal inflammatory disorders are expected to range from about 2 to about 60 mg/day of the compound of formula (I), including from about 4 to about 50 mg/day and from about 4 to about 40 mg per day for an average 70 kg human.

Combination Therapy

Compounds of the invention may also be used in combination with one or more agents which act by the same mechanism or by different mechanisms to effect treatment of gastrointestinal inflammatory disorders. Useful classes of agents for combination therapy include, but are not limited to, aminosalicylates, steroids, systemic immunosuppressants, anti-TNFα antibodies, anti-alpha4 (anti-VLA-4) antibodies, anti-integrin $\alpha_4\beta_7$ antibodies, anti-bacterial agents, and anti-diarrheal medicines.

Aminosalicylates that may be used in combination with the present compounds include, but are not limited to, mesalamine, olsalazine and sulfasalazine. Examples of steroids include, but are not limited to, prednisone, prednisolone, hydrocortisone, budesonide, beclomethasone, and fluticasone. Systemic immunosuppressants useful for treatment of inflammatory disorders include, but are not limited to cyclosporine, azathioprine, methotrexate, 6-mercaptopurine, and tacrolimus. Further, anti-TNFα antibodies, which include, but are not limited to, infliximab, adalimumab, golimumab, and certolizumab, may be used in combination therapy. Useful compounds acting by other mechanisms include anti-alpha4 antibodies, such as natalizumab, anti-integrin $\alpha_4\beta_7$ antibodies, such as vedolizumab, anti-bacterial agents, such as rifaximin, and anti-diarrheal medicines, such as loperamide. (Mozaffari et al. *Expert Opin. Biol. Ther.* 2014, 14, 583-600; Danese, *Gut,* 2012, 61, 918-932; Lam et al., *Immunotherapy,* 2014, 6, 963-971.)

In another aspect, therefore, the invention provides a therapeutic combination for use in the treatment of gastrointestinal inflammatory disorders, the combination comprising a compound of the invention and one or more other therapeutic agents useful for treating gastrointestinal inflammatory disorders. For example, the invention provides a combination comprising a compound of the invention and one or more agents selected from aminosalicylates, steroids, systemic immunosuppressants, anti-TNFα antibodies, anti-alpha4 antibodies, anti-integrin $\alpha_4\beta_7$ antibodies, anti-bacterial agents, and anti-diarrheal medicines. Secondary agent(s), when included, are present in a therapeutically effective amount, i.e. in any amount that produces a therapeutically beneficial effect when co-administered with a compound of the invention.

Further, in a method aspect, the invention provides a method of treating gastrointestinal inflammatory disorders, the method comprising administering to the mammal a compound of the invention and one or more other therapeutic agents useful for treating gastrointestinal inflammatory disorders.

When used in combination therapy, the agents may be formulated in a single pharmaceutical composition, as disclosed above, or the agents may be provided in separate compositions that are administered simultaneously or at separate times, by the same or by different routes of administration. When administered separately, the agents are administered sufficiently close in time so as to provide a desired therapeutic effect. Such compositions can be packaged separately or may be packaged together as a kit. The two or more therapeutic agents in the kit may be administered by the same route of administration or by different routes of administration.

EXAMPLES

The following synthetic and biological examples are offered to illustrate the invention, and are not to be construed in any way as limiting the scope of the invention.

In the examples below, the following abbreviations have the following meanings unless otherwise indicated. Abbreviations not defined below have their generally accepted meanings.

Ac=acetyl
ACN=acetonitrile
alloc=allyloxycarbonyl d=day(s)
DCM=dichloromethane
DIPEA=N,N-diisopropylethylamine
DMAP=4-dimethylaminopyridine
Et$_3$N=triethylamine
EtOAc=ethyl acetate
EtOH=ethanol
h=hour(s)
IPA=isopropyl alcohol
MeOH=methanol
min=minute(s)
RT=room temperature
tBu=tert-butyl
TFA=trifluoroacetic acid
THF=tetrahydrofuran Reagents and solvents were purchased from commercial suppliers (Sigma-Aldrich, Fluka, etc.), and used without further purification. Progress of reaction mixtures was monitored by thin layer chromatography (TLC), analytical high performance liquid chromatography (anal. HPLC), and mass spectrometry. Reaction mixtures were worked up as described specifically in each reaction; commonly they were purified by extraction and other purification methods such as temperature-, and solvent-dependent crystallization, and precipitation. In addition, reaction mixtures were routinely purified by column chromatography or by preparative HPLC, typically using C18 or BDS column packings and conventional eluents. Typical preparative HPLC conditions are described below.

Characterization of reaction products was routinely carried out by mass spectrometry and analytical HPLC. Mass spectrometric identification of compounds was performed by an electrospray ionization method (ESMS) with an Applied Biosystems (Foster City, Calif.) model API 150 EX instrument or a Waters (Milford, Mass.) 3100 instrument, coupled to autopurification systems.

Preparative HPLC Conditions
Column: C18, 5 µm. 21.2×150 mm or C18, 5 µm 21×250 or C14, 5 µm 21×150 mm
Column temperature: Room Temperature
Flow rate: 20.0 mL/min
Mobile Phases: A=Water+0.05% TFA
  B=ACN+0.05% TFA,
Injection volume: (100-1500 µL)
Detector wavelength: 214 nm Crude compounds were dissolved in 1:1 water:acetic acid at about 50 mg/mL. A 4 minute analytical scale test run was carried out using a 2.1×50 mm C18 column followed by a 15 or 20 minute preparative scale run using 100 µL injection with the gradient based on the % B retention of the analytical scale test run. Exact gradients were sample dependent. Samples with close running impurities were checked with a 21×250 mm C18 column and/or a 21×150 mm C14 column for best separation. Fractions containing desired product were identified by mass spectrometric analysis.

Analytical HPLC Conditions
Method A
Instrument: Agilent 1260 HPLC
Column: LUNA C18 (2), 150×4.60 mm, 3 micron
Column temperature: 35° C.
Flow rate: 1.2 mL/min
Injection volume: 5 µL
Sample preparation: Dissolve in 1:1 ACN:water to ~0.5 mg/mL solution
Mobile Phases: A=Water:ACN:TFA (98:2:0.05)
  B=Water:ACN:TFA (30:70:0.05)
Detector wavelength: 230 nm
Gradient: 28 min total (time (min)/% B): 0/10, 20/100, 22/100, 23/10, 28/10

Method B
Instrument: Agilent 1260 HPLC
Column: Zorbax-Bonus RP C14, 30×2.1 mm, 1.8 micron
Column temperature: 60° C.
Flow rate: 1.2 mL/min
Injection volume: 3 µL
Sample preparation: Dissolve in 1:1 ACN:water to ~1.0 mg/mL solution
Mobile Phases: A=Water:TFA (99.9%:0.1%)
  B=ACN:TFA (99.9%:0.1%)
Detector wavelength: 214 nm
Gradient: 3.0 min total (time (min)/% B): 0/5, 1.5/65, 1.8/95, 2.1/95, 2.5/5, 3.0/5

Preparation 1 (2S,3R,4S,5S,6S)-2-(4-(hydroxymethyl)-2-nitrophenoxy)-6-(methoxycarbonyl)tetrahydro-2H-pyran-3,4,5-triyl triacetate (10)

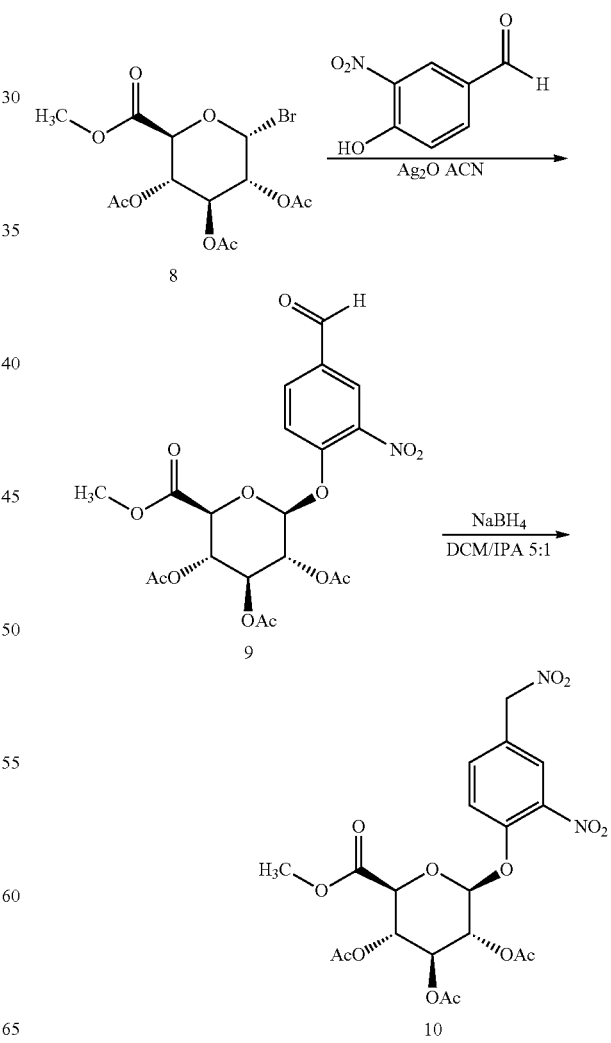

(a) (2S,3R,4S,5S,6S)-2-(4-formyl-2-nitrophenoxy)-6-(methoxycarbonyl)tetrahydro-2H-pyran-3,4,5-triyl triacetate (9)

To a 2 L 3-neck flask equipped with a mechanical stirrer was added (2R,3R,4S,5S,6S)-2-bromo-6-(methoxycarbonyl)tetrahydro-2H-pyran-3,4,5-triyl triacetate (8) (51 g, 128.4 mmol), 4-hydroxy-3-nitrobenzaldehyde (20.98 g, 125.5 mmol), and silver oxide (37.7 g, 162.7 mmol), followed by ACN (750 mL). The reaction mixture was stirred in the dark for 18 h and filtered through diatomaceous earth (Celite®). The solid was washed with ACN (3×100 mL) and the filtrate was distilled under reduced pressure to 100 mL. To the filtrate was added EtOAc (1750 mL) and sat. sodium bicarbonate (1 L) and the reaction mixture was stirred at RT for 30 min, filtered through Celite and allowed to settle. The organic layer was washed with sat. sodium bicarbonate (1 L) and brine (1 L), dried over sodium sulfate (100 g) for 2 h, filtered and distilled under reduced pressure to dryness to provide crude Compound 9 as a yellow solid (55 g, 90% yield, 97.4% purity) HPLC Retention time 15.61 min.

(b) (2S,3R,4S,5S,6S)-2-(4-(hydroxymethyl)-2-nitrophenoxy)-6-(methoxycarbonyl)tetrahydro-2H-pyran-3,4,5-triyl triacetate (10)

To a 1 L 3-neck flask equipped with a mechanical stirrer was added Compound 9 (32.7 g, 67.6 mmol) followed by DCM (350 mL) and IPA (70 mL). The reaction mixture was stirred to dissolve the solid and then cooled to 0° C. To the solution was added sodium borohydride (1.54 g, 40.6 mmol) in three portions, keeping the temperature below 5° C., and the reaction mixture was stirred at 0° C. for 1 h and slowly poured into ice water (400 mL). To the solution was added DCM (350 mL) and the mixture was stirred for 30 min, allowed to settle for 30 min and the layers were separated. The aqueous layer was back extracted with DCM (100 mL). The combined organic layers were washed with brine (500 mL). After 30 min, the layers were separated and the brine layer was back extracted with DCM (100 mL). The combined organic layers were dried over sodium sulfate (50 g) for 2 h, filtered through Celite, and distilled under reduced pressure to dryness. The resulting solid was stirred with 95% denatured EtOH (130 mL) at 50° C. for 30 min and at RT for 12 h to form a crystalline solid which was washed with EtOH (30 mL) and dried under vacuum at RT for 16 h to provide the title compound as a white solid (21 g, 66% yield 98% purity) HPLC Method A Retention time 13.18 min.

Preparation 2: (2S,3S,4S,5R,6S)-2-(methoxycarbonyl)-6-(4-(((methyl(2-(methylamino)ethyl)carbamoyl)oxy)methyl)-2-nitrophenoxy)tetrahydro-2H-pyran-3,4,5-triyl triacetate (12)

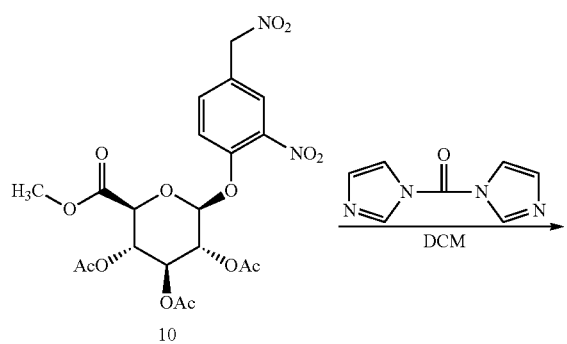

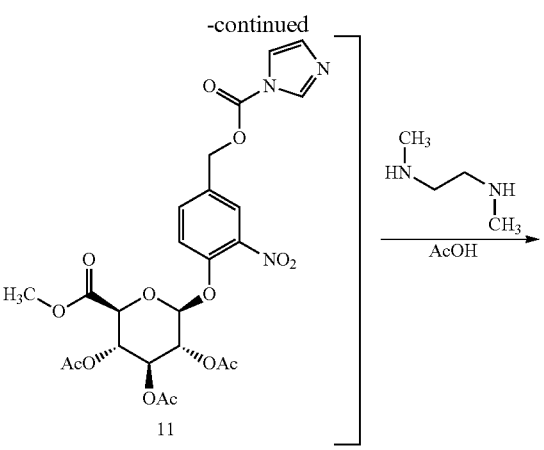

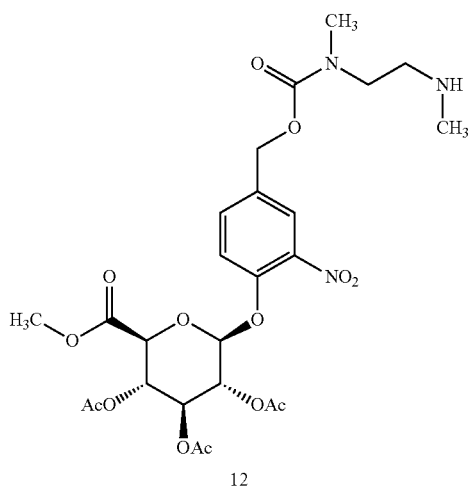

To a 100 mL flask equipped with a magnetic stirrer was added (2S,3R,4S,5S,6S)-2-(4-(hydroxymethyl)-2-nitrophenoxy)-6-(methoxycarbonyl)tetrahydro-2H-pyran-3,4,5-triyltriacetate (10) (4.86 g, 10 mmol) and carbonyldiimidazole (2.11 g, 13 mmol) followed by DCM (50 mL). The reaction mixture was stirred at RT for 3 h to form a solution of (2S,3R,4S,5S,6S)-2-(4-(((1H-imidazole-1-carbonyl)oxy)methyl)-2-nitrophenoxy)-6-(methoxycarbonyl)tetrahydro-2H-pyran-3,4,5-triyltriacetate (11).

To a 250 mL 3-neck flask equipped with a magnetic stirrer was added $N^1,N^2$-dimethylethane-1,2-diamine (3.09 g, 35 mmol, 3.76 mL) followed by DCM (30 mL). The reaction mixture was cooled to 0° C. and acetic acid (2.1 g, 35 mmol, 2 mL) was added slowly at <5° C. to form a suspension. To the suspension was slowly added the solution of intermediate 11; the reaction mixture was stirred at 0-5° C. for 30 min and then at RT for 3 h. DCM (30 mL) and water (60 mL) were added and the reaction mixture was stirred at RT for 10 min. The organic layer was washed with water (2×60 mL), dried over sodium sulfate for 2 h and filtered to provide the title compound in solution (~70% yield), which was stored at 0-4° C. and used without purification. HPLC Method A Retention time 11.04 min.

Preparation 3: (2S,3R,4S,5S,6S)-2-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)-2-nitrophenoxy)-6-(methoxycarbonyl)tetrahydro-2H-pyran-3,4,5-triyl triacetate (14)
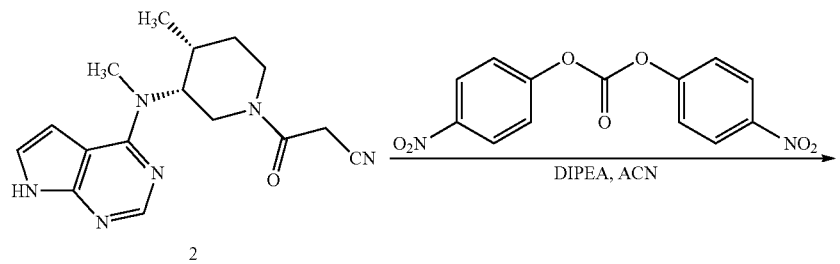
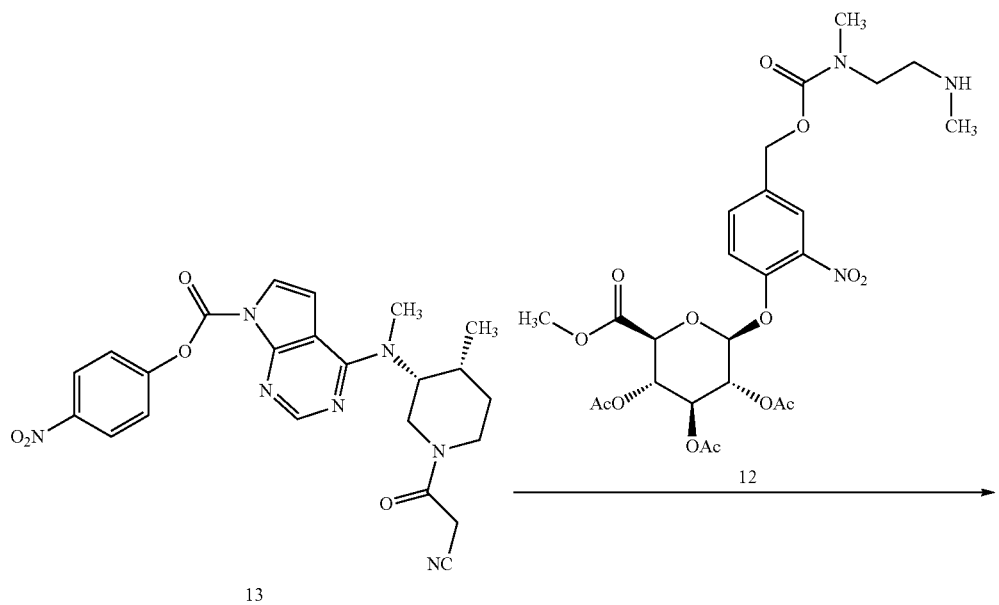
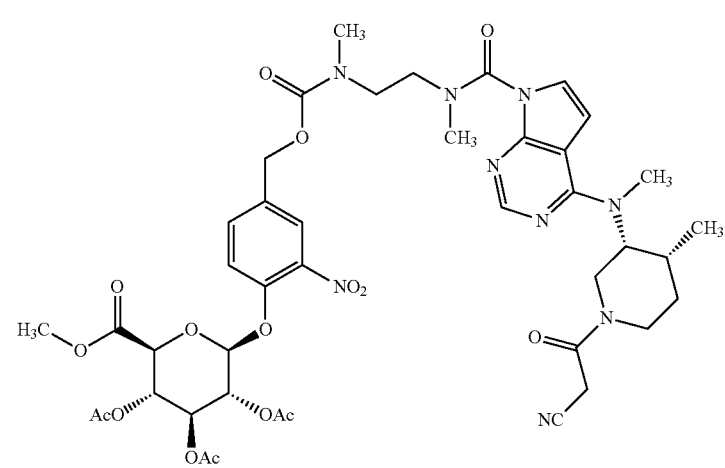

To a 1 L 3-neck flask equipped with a magnetic stirrer was added 3-((3R,4R)-4-methyl-3-(methyl(7H-pyrrolo[2,3-d]pyrimidin-4-yl)amino)piperidin-1-yl)-3-oxopropanenitrile (2) (9.65 g, 31 mmol), bis(4-nitrophenyl) carbonate (12.22 g, 40 mmol), and ACN (240 mL) and the reaction mixture was cooled to 0° C. DIPEA (5.59 g, 43 mmol) was added dropwise and the reaction mixture was stirred at RT for 4 h and cooled to 0° C. To the cooled reaction mixture was added a solution of (2S,3S,4S,5R,6S)-2-(methoxycarbonyl)-6-(4-(((methyl(2-(methylamino)ethyl)-carbamoyl)oxy)methyl)-2-nitrophenoxy)tetrahydro-2H-pyran-3,4,5-triyltriacetate (12) in DCM (350 mL, 30 mmol) at <10° C. and the reaction mixture was stirred at 15° C. for 1 h and then quenched with acetic acid (2.5 g, 42 mmol). DCM (200 mL) and water (300 mL) were added, the layers were separated, and the organic layer was washed with 3% sodium carbonate (2×350 mL) and then with 0.5 M HCl (2×200 mL) and with 10% sodium chloride (200 mL), and dried over sodium sulfate (50 g) for 5 h, filtered, and concentrated to ~100 mL. The concentrated solution was purified by silica gel chromatography (600 g silica column, flow rate 60 mL/min, gradient: 40% DCM in EtOAc to 100% EtOAc over 5 min, 100% EtOAc for 60 min, 3% MeOH to 5% MeOH in EtOAc over 30 min, 5% MeOH in EtOAc to completion). Pure fractions were combined and distilled to dryness under vacuum to provide the title compound (21.2 g, 97% purity, 73% yield). HPLC Method A Retention time 13.92 min.

Example 1: (2S,3S,4S,5R,6S)-6-(4-((((2-(4-((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)-2-nitrophenoxy)-3,4,5-trihydroxytetrahydro-2H-pyran-2-carboxylic acid (1)

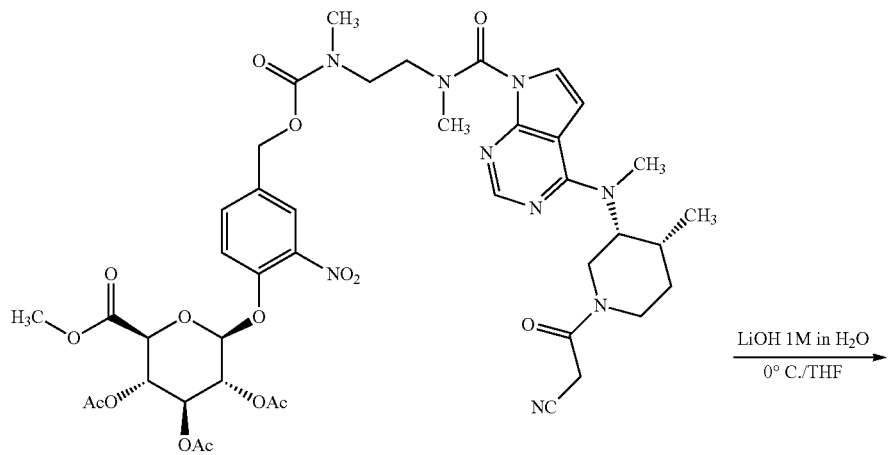

14

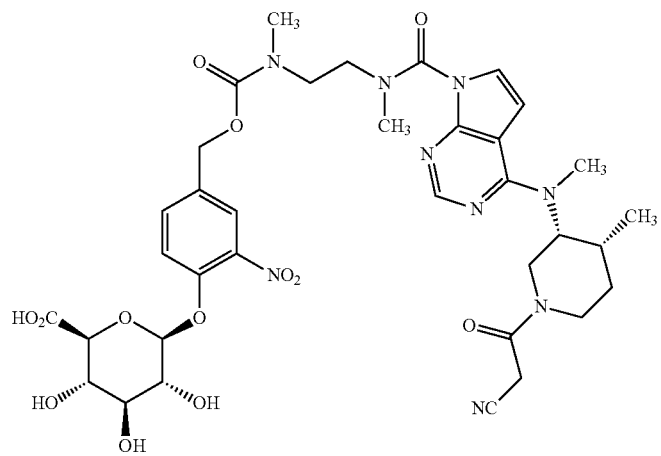

1

To a 500 mL 3-neck flask equipped with a magnetic stirrer was added (2S,3R,4S,5S,6S)-2-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)-2-nitrophenoxy)-6-(methoxycarbonyl)tetrahydro-2H-pyran-3,4,5-triyltriacetate (14) (20.9 g, 22 mmol) and THF (210 mL). The reaction mixture was cooled to 0° C. and 1 M LiOH in water (46 mL, 47 mmol) was added over 20 min and the reaction mixture was stirred for 20 min. A second equal portion of LiOH solution was added over 30 min and the reaction mixture was stirred for 2 h. Acetic acid (5.6 g, 93 mmol) was added and the reaction mixture was transferred to a 2 L round bottom flask. To the flask was added ACN (500 mL) and the mixture was distilled under reduced pressure to remove 600 mL of solvent. The process was repeated twice with the third distillation continued to dryness. The resulting solid was dissolved in 2% ACN in water (350 mL) and purified in 90 mL batches by reverse phase chromatography (450 g C-18 silica column, flow rate 40 mL/min, Solvent A: 0.5% acetic acid in water; Solvent B: ACN, gradient: 110 min total (time (min)/% B): 0/2, 10/2, 100/28, 110/28 followed by wash 90% B. Product fractions were combined, the procedure repeated three times, and the combined fractions concentrated to about 600 mL and lyophilized to provide the title compound as a solid (11.2 g, 60% yield, 99% purity). HPLC Method A Retention time 7.95 min.

Example 2 (2S,3S,4S,5R,6S)-6-(2-amino-4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenoxy)-3,4,5-trihydroxytetrahydro-2H-pyran-2-carboxylic acid (3)

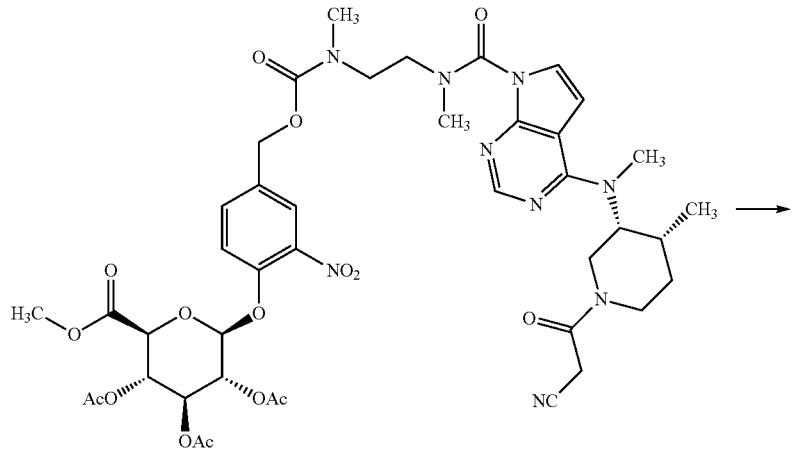

14

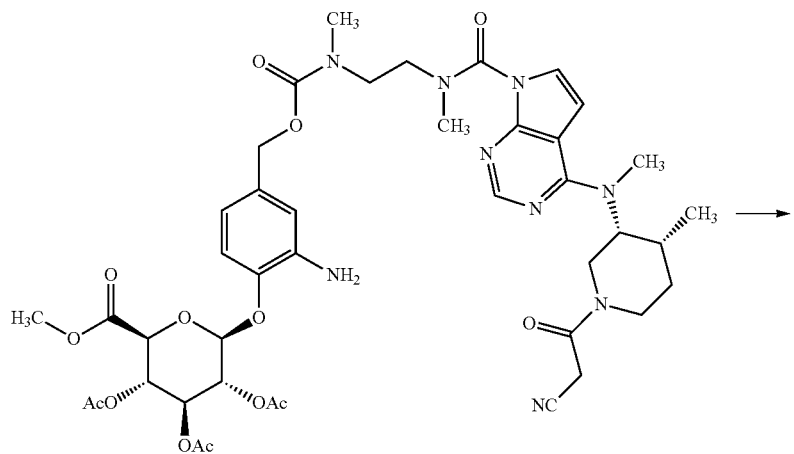

15

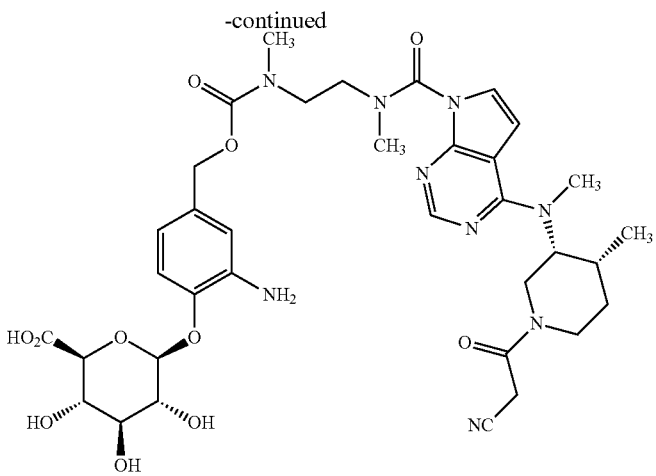

3

(a) (2S,3R,4S,5S,6S)-2-(2-amino-4-(((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenoxy)-6-(methoxycarbonyl)tetrahydro-2H-pyran-3,4,5-triyltriacetate (15)

To a solution of (2S,3R,4S,5S,6S)-2-(4-(((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)-2-nitrophenoxy)-6-(methoxycarbonyl)tetrahydro-2H-pyran-3,4,5-triyltriacetate (14) (1.55 g, 1.65 mmol) in EtOH (50 mL) was added palladium hydroxide on carbon (11.57 mg, 0.08 mmol). The reaction solution was stirred under hydrogen atmosphere at room temperature for 3 d, filtered through a pad of Celite, washed with EtOH, and concentrated in vacuo. The crude material was isolated as a brown foam and was used without further purification. (m/z): [M+H]$^+$ calcd for $C_{42}H_{53}N_9O_{14}$ 908.37 found 908.8.

(b) (2S,3S,4S,5R,6S)-6-(2-amino-4-(((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenoxy)-3,4,5-trihydroxytetrahydro-2H-pyran-2-carboxylic acid (3)

To a solution of the product of the previous step (0.95 g, 1.05 mmol) in a 1:1:1 mixture of MeOH (3.49 mL), THF (3.49 mL) and water (3.49 mL) was added LiOH (63 mg, 2.62 mmol) and the mixture was stirred at room temperature for 1 h. The reaction solution was concentrated in vacuo and the crude material was purified by reverse phase column chromatography to afford the title compound (96 mg, 12% yield) as a white solid. HPLC Method B Retention time 0.85 min.

Preparation 4: 4-nitrophenyl 4-(((3R,4R)-1-(2-cyanoacetyl)-4-methylpiperidin-3-yl)(methyl)amino)-7H-pyrrolo[2,3-d]pyrimidine-7-carboxylate (13)

To a solution of 3-((3R,4R)-4-methyl-3-(methyl(7H-pyrrolo[2,3-d]pyrimidin-4-yl)amino)piperidin-1-yl)-3-oxopropanenitrile (2) (0.75 g, 2.40 mmol) in DCM (12 mL) was added a solution of sodium hydroxide (0.29 g, 7.20 mmol) in water (4.00 mL) and tetrabutylamonium bromide (0.08 g, 0.24 mmol). A solution of 4-nitrophenyl chloroformate (0.97 g, 4.80 mmol) in DCM (4 mL) was slowly added. The reaction mixture was stirred at RT for 1 h, extracted with DCM, and the organic layer was washed with satd. ammoniun chloride solution and brine, dried over sodium sulfate, filtered and concentrated in vacuo. The crude residue was purified by column chromatography (0-100% EtOAc in hexanes) to afford title compound (0.94 g, 82%) as a light yellow solid. (m/z): [M+H]$^+$ calcd for $C_{23}H_{23}N_7O_5$ 478.18 found 478.2.

Preparation 5: (2S,3S,4S,5R,6S)-2-(methoxycarbonyl)-6-(4-(((methyl(2-(methylamino)ethyl)carbamoyl)oxy)methyl)phenoxy)tetrahydro-2H-pyran-3,4,5-triyl triacetate (18)

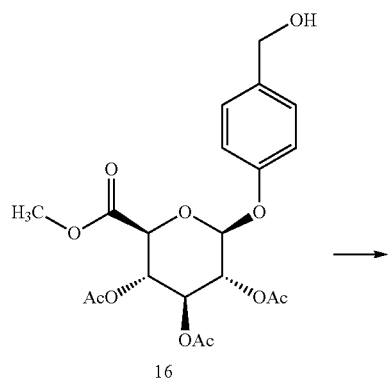

16

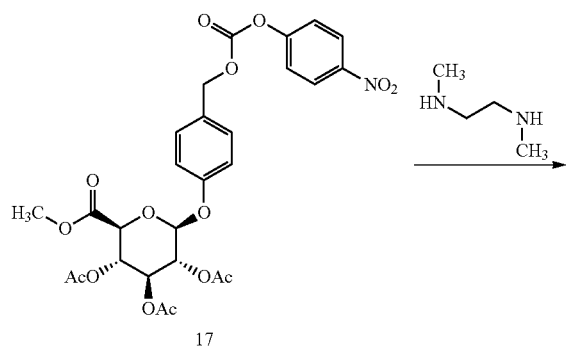

17

(a) (2S,3S,4S,5R,6S)-2-(methoxycarbonyl)-6-(4-(((((4-nitrophenoxy)carbonyl)oxy)methyl) phenoxy)tetrahydro-2H-pyran-3,4,5-triyltriacetate (17)

To a solution of (2S,3R,4S,5S,6S)-2-(4-(hydroxymethyl)phenoxy)-6-(methoxycarbonyl)tetrahydro-2H-pyran-3,4,5-triyltriacetate (16) (27.0 g, 61.3 mmol) and Et$_3$N (25.5 mL, 17.0 mmol) in DCM (250 mL) was slowly added a solution of p-nitrophenyl chloroformate (18.53 g, 91.9 mmol) in DCM (100 mL). The solution was stirred at RT for 1 h, diluted with water (100 mL) and extracted with DCM (3×100 mL). The combined organic layers were concentrated under reduced pressure and the crude residue was purified by column chromatography (35% EtOAc in hexanes) to afford the title compound (37.0 g, 56% yield).

(b) (2S,3S,4S,5R,6S)-2-(methoxycarbonyl)-6-(4-(((methyl(2-(methylamino)ethyl)carbamoyl)oxy)methyl)phenoxy)tetrahydro-2H-pyran-3,4,5-triyl triacetate (18)

To a solution of (2S,3S,4S,5R,6S)-2-(methoxycarbonyl)-6-(4-(((((4-nitrophenoxy)carbonyl)oxy)methyl)phenoxy)tetrahydro-2H-pyran-3,4,5-triyltriacetate (17) (0.50 g, 0.83 mmol) in DCM (8.26 mL) at RT was added N',N$^2$-dimethylethane-1,2-diamine (0.44 mL, 4.13 mmol). After 1.5 h, the reaction solution was filtered and washed with DCM. The filtrate was concentrated in vacuo and the residue was purified by column chromatography (0-10% MeOH in DCM) to afford the title compound (354 mg, 77% yield) as a colored solid. (m/z): [M+H]$^+$ calcd for C$_{25}$H$_{34}$N$_2$O$_{12}$ 555.21 found 555.6.

The following intermediates were prepared by a process analogous to Preparation

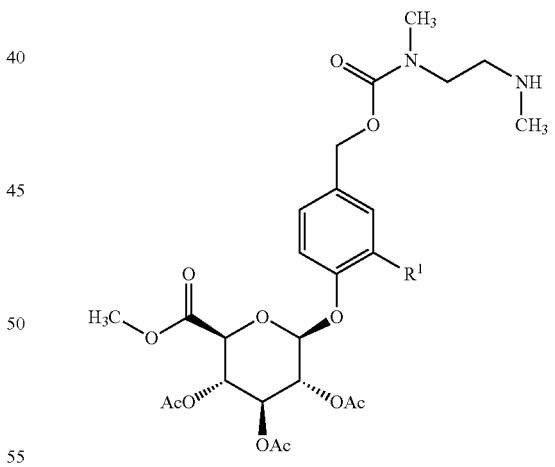

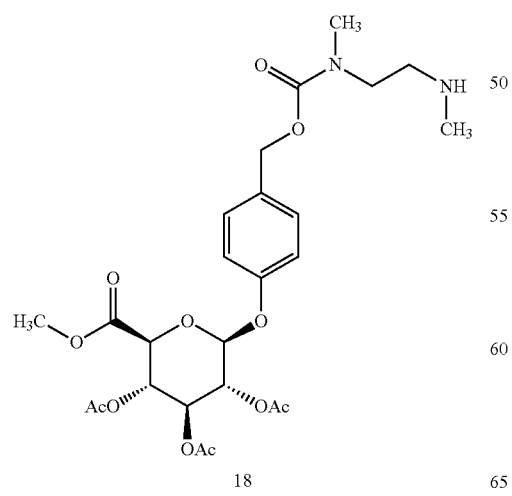

18

| R$^1$ | Compound No. | |
|---|---|---|
| methyl | 19 | (m/z): [M + H]$^+$ calcd for C$_{26}$H$_{36}$N$_2$O$_{12}$ 569.23 found 569.7 |
| chloro | 20 | (m/z): [M + H]$^+$ calcd for C$_{25}$H$_{33}$ClN$_2$O$_{12}$ 591.17 found 591.4 |
| methoxy | 21 | (m/z): [M + H]$^+$ calcd for C$_{26}$H$_{36}$N$_2$O$_{13}$ 585.22 found 585.5 |

Example 3: (2S,3S,4S,5R,6S)-6-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenoxy)-3,4,5-trihydroxytetrahydro-2H-pyran-2-carboxylic acid (4)
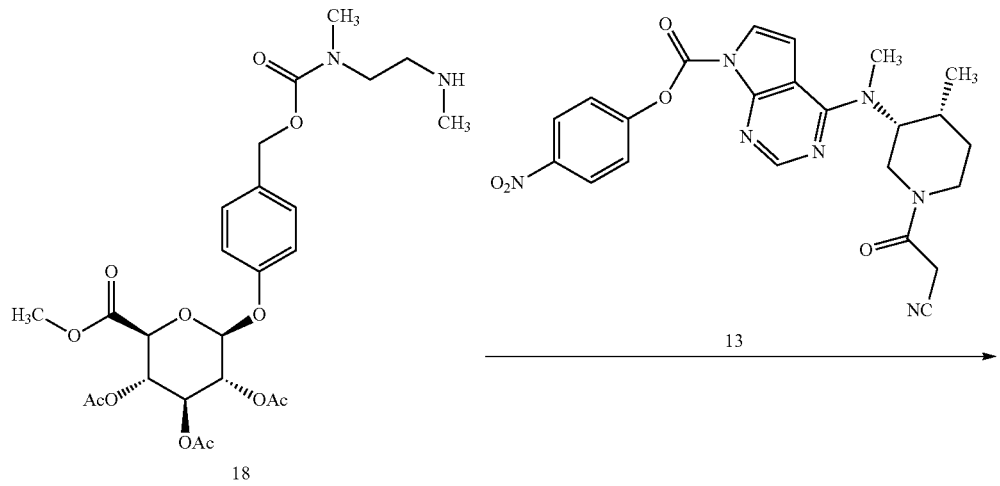
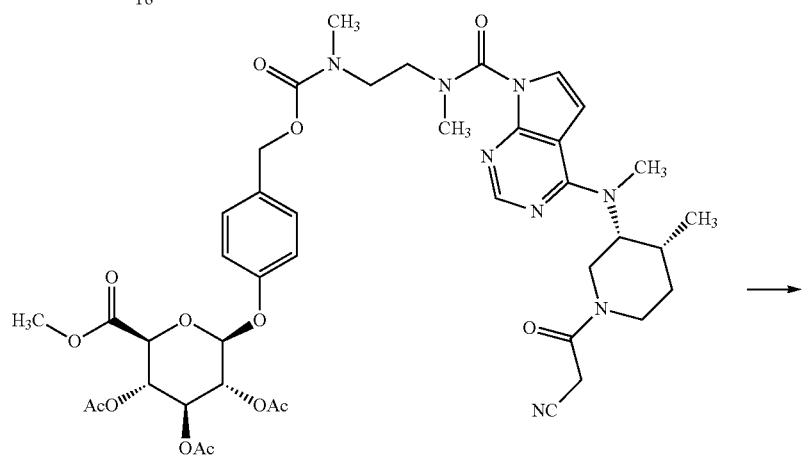
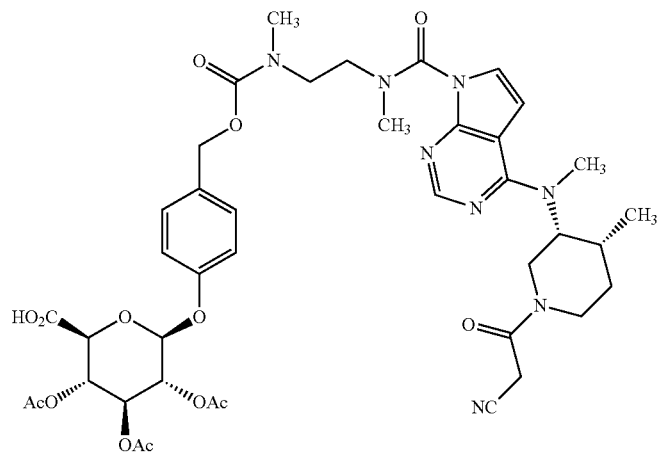

(a) (2S,3R,4S,5S,6S)-2-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)-(methyl)carbamoyl)oxy)methyl)phenoxy)-6-(methoxycarbonyl)tetrahydro-2H-pyran-3,4,5-triyltriacetate (22)

To a solution of (2S,3S,4S,5R,6S)-2-(methoxycarbonyl)-6-(4-(((methyl(2-(methylamino)ethyl)carbamoyl)oxy)methyl)phenoxy)tetrahydro-2H-pyran-3,4,5-triyl triacetate (18) (0.35 g, 0.63 mmol) and 4-nitrophenyl 4-(((3R,4R)-1-(2-cyanoacetyl)-4-methylpiperidin-3-yl)(methyl)amino)-7H-pyrrolo[2,3-d]pyrimidine-7-carboxylate (13) (0.30 g, 0.63 mmol) in DMF (5.05 mL) was added Et$_3$N (0.13 mL, 0.95 mmol) and the resulting mixture was stirred at 40° C. After 1.5 h, LC/MS indicated clean product formation. The reaction solution was cooled to room temperature and concentrated in vacuo. The crude product was isolated as a yellow residue which was used without further purification. (m/z): [M+H]$^+$ calcd for C$_{42}$H$_{52}$H$_8$O$_{14}$ 893.36 found 893.9.

(b) (2S,3S,4S,5R,6S)-6-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenoxy)-3,4,5-trihydroxytetrahydro-2H-pyran-2-carboxylic acid (4)

To a solution of the product of the previous step (0.56 g, 0.63 mmol) in a 1:1:1 mixture of MeOH (2.10 mL), THF (2.10 mL) and water (2.10 mL) was added LiOH (40 mg, 1.70 mmol) and the solution was stirred at RT, concentrated in vacuo and the crude residue was purified by reverse phase column chromatography to afford the title compound (0.12 g, 27%) as a white solid. (m/z): [M+H]$^+$ calcd for C$_{35}$H$_{44}$H$_8$O$_{11}$ 753.31 found 753.8. HPLC Method B Retention time 0.98 min.

Example 4: (2S,3S,4S,5R,6S)-6-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)-2-methylphenoxy)-3,4,5-trihydroxytetrahydro-2H-pyran-2-carboxylic acid (5)

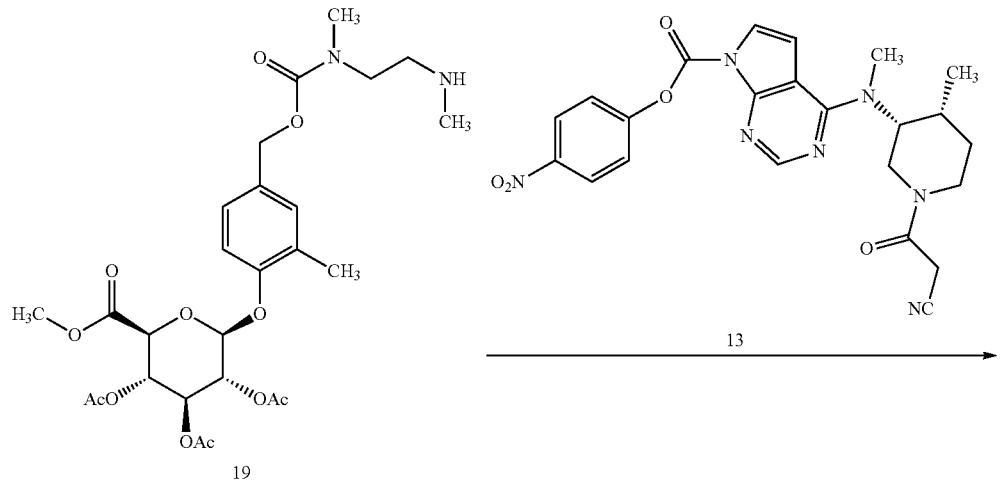

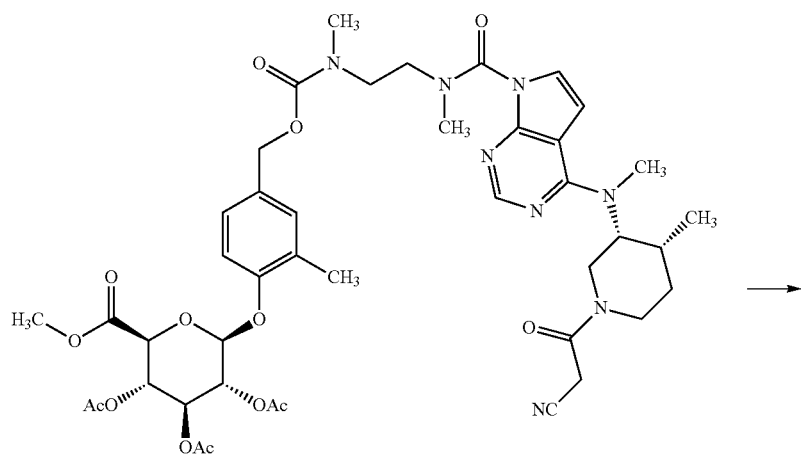

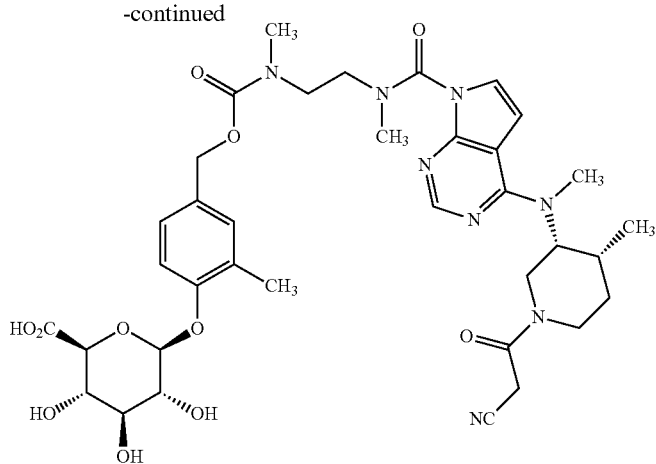

5

(a) (2S,3R,4S,5S,6S)-2-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)-(methyl)carbamoyl)oxy)methyl)-2-methylphenoxy)-6-(methoxycarbonyl)tetrahydro-2H-pyran-3,4,5-triyltriacetate (23)

To a solution of (2S,3S,4S,5R,6S)-2-(methoxycarbonyl)-6-(2-methyl-4-(((methyl(2-(methylamino)ethyl)carbamoyl)oxy)methyl)phenoxy)tetrahydro-2H-pyran-3,4,5-triyltriacetate (19) (0.46 g, 0.81 mmol) in DCM (8.00 mL) was slowly added a solution of 4-nitrophenyl 4-(((3R,4R)-1-(2-cyanoacetyl)-4-methylpiperidin-3-yl)(methyl)amino)-7H-pyrrolo[2,3-d]pyrimidine-7-carboxylate (13) (0.39 g, 0.81 mmol) in DCM (3.00 mL) and the solution was stirred at RT for 1.5 h, concentrated in vacuo and the yellow solid was used without further purification. (m/z): [M+H]+ calcd for $C_{43}H_{54}H_8O_{14}$ 907.38 found 907.6.

(b) (2S,3S,4S,5R,6S)-6-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)-2-methylphenoxy)-3,4,5-trihydroxytetrahydro-2H-pyran-2-carboxylic acid (5)

To an ice-cold solution of the product of the previous step (0.73 g, 0.81 mmol) in MeOH (29 mL) was slowly added an aqueous solution of LiOH (4.04 mL, 4.04 mmol). After stirring at 0° C. for 1.5 h, the reaction solution was adjusted to pH 5-6 by the slow addition of 1 N HCl. The reaction solution was concentrated in vacuo and the crude material was purified by reverse phase column chromatography to afford the title compound (0.47 g, 76% yield) as a white solid. (m/z): [M+H]+ calcd for $C_{36}H_{46}H_8O_{11}$ 767.33 found 767.8. HPLC Method B Retention time 1.02 min.

Example 5: (2S,3S,4S,5R,6S)-6-(2-chloro-4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenoxy)-3,4,5-trihydroxytetrahydro-2H-pyran-2-carboxylic acid (6)

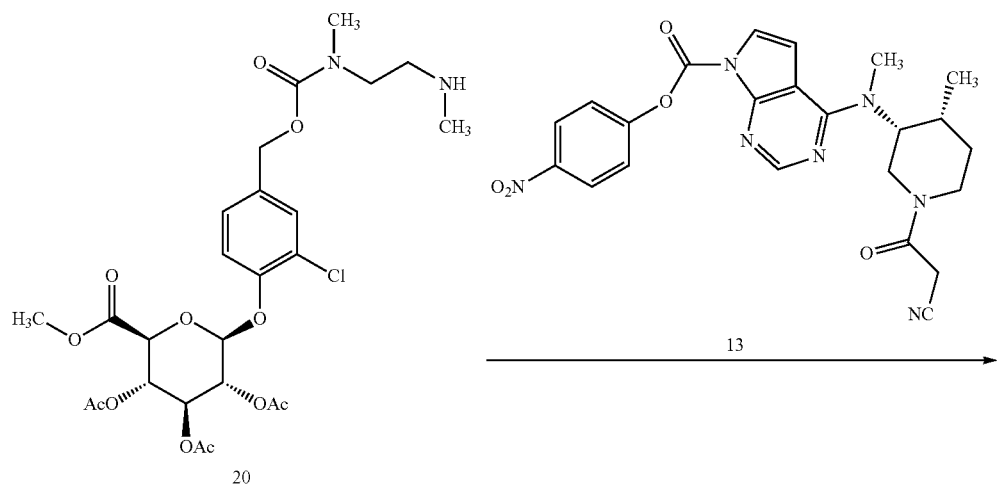

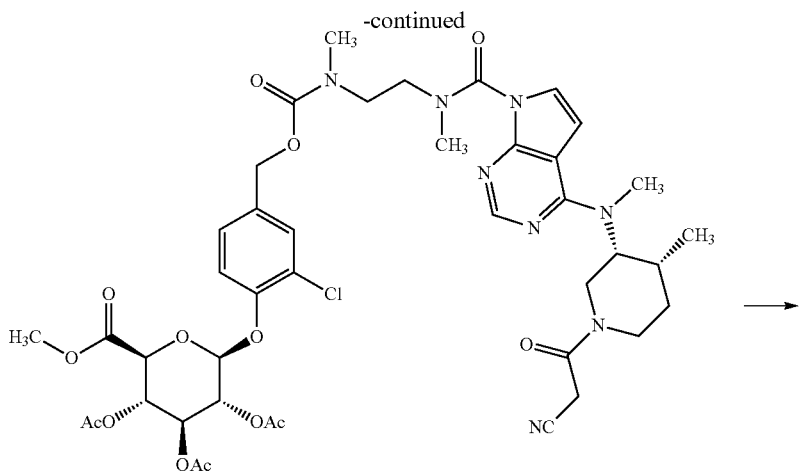

23

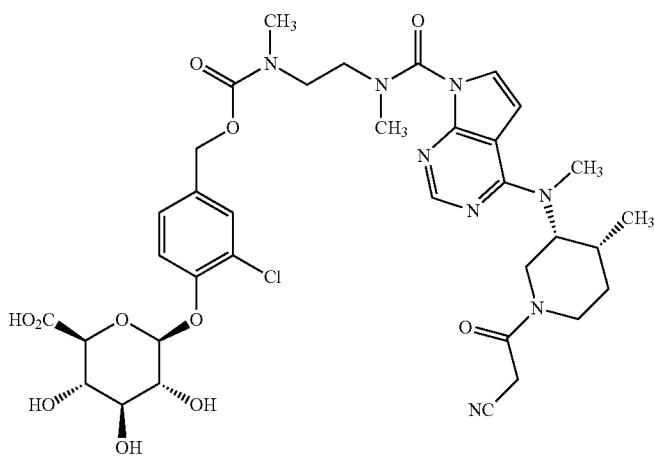

6

(a) (2S,3R,4S,5S,6S)-2-(2-chloro-4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenoxy)-6-(methoxycarbonyl)tetrahydro-2H-pyran-3,4,5-triyl triacetate (24)

To a solution of (2S,3R,4S,5S,6S)-2-(2-chloro-4-(((methyl(2-(methylamino)ethyl)-carbamoyl)oxy)methyl)phenoxy)-6-(methoxycarbonyl)tetrahydro-2H-pyran-3,4,5-triyl triacetate (20) (0.33 g, 0.57 mmol) and 4-nitrophenyl 4-(((3R,4R)-1-(2-cyanoacetyl)-4-methylpiperidin-3-yl)(methyl)amino)-7H-pyrrolo[2,3-d]pyrimidine-7-carboxylate (13) (0.27 g, 0.57 mmol) in DMF (4.52 mL) was added Et$_3$N (0.12 mL, 0.85 mmol) and the resulting solution was stirred at 40° C. After 1 h, the solution was concentrated in vacuo. The product was isolated as a yellow residue which was used without further purification. (m/z): [M+H]$^+$ calcd for C$_{42}$H$_{51}$ClN$_8$O$_{14}$ 927.32 found 927.7.

(b) (2S,3S,4S,5R,6S)-6-(2-chloro-4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenoxy)-3,4,5-trihydroxytetrahydro-2H-pyran-2-carboxylic acid (6)

To a solution of (2S,3R,4S,5S,6S)-2-(2-chloro-4-(((((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenoxy)-6-(methoxycarbonyl)tetrahydro-2H-pyran-3,4,5-triyl triacetate (0.52 g, 0.57 mmol) in a 1:1:1 mixture of MeOH (1.88 mL), THF (1.88 mL) and water (1.88 mL) was added LiOH (40 mg, 1.53 mmol) and the solution was stirred at room temperature for 2 h. The reaction solution was concentrated in vacuo and the crude material was purified by reverse phase column chromatography to afford the final product (0.22 g, 49%) as a white solid. (m/z): [M+H]$^+$ calcd for C$_{35}$H$_{43}$ClN$_8$O$_{11}$ 787.27 found 787.8. HPLC Method B Retention time 1.04 min.

Example 6: (2S,3S,4S,5R,6S)-6-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)-2-methoxyphenoxy)-3,4,5-trihydroxytetrahydro-2H-pyran-2-carboxylic acid (7)
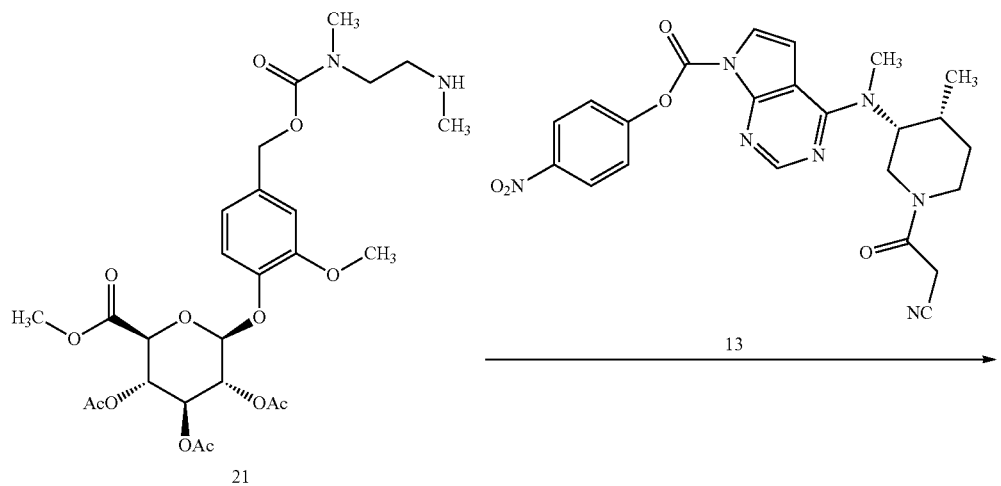
21
13
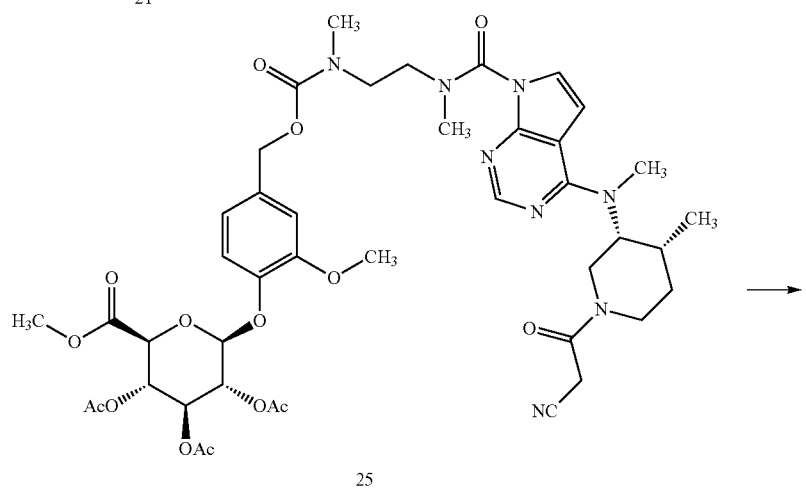
25
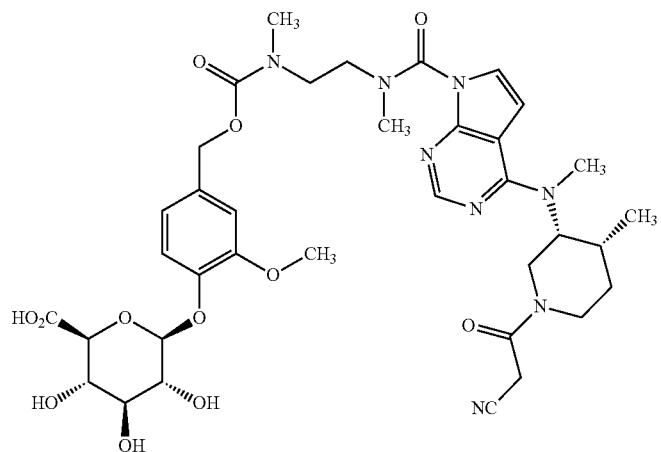
7

(a) (2S,3R,4S,5S,6S)-2-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)-2-methoxyphenoxy)-6-(methoxycarbonyl)tetrahydro-2H-pyran-3,4,5-triyl triacetate (25)

To a solution of (2S,3R,4S,5S,6S)-2-(2-methoxy-4-(((methyl(2-(methylamino)ethyl)carbamoyl)oxy)methyl)phenoxy)-6-(methoxycarbonyl)tetrahydro-2H-pyran-3,4,5-triyl triacetate (21) (0.60 g, 1.02 mmol) in DCM (10.00 mL) was slowly added a solution of 4-nitrophenyl 4-(((3R,4R)-1-(2-cyanoacetyl)-4-methylpiperidin-3-yl)(methyl)amino)-7H-pyrrolo[2,3-d]pyrimidine-7-carboxylate (13) (0.49 g, 1.02 mmol) in DCM (3.00 mL) and the resulting mixture was stirred at RT for 1.5 h. The reaction solution was concentrated in vacuo and the resulting yellow solid was used without further purification. (m/z): [M+H]$^+$ calcd for $C_{43}H_{54}H_8O_{15}$ 923.37 found 924.1.

(b) (2S,3S,4S,5R,6S)-6-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)-2-methoxyphenoxy)-3,4,5-trihydroxytetrahydro-2H-pyran-2-carboxylic acid (7)

To an ice-cold solution of the product of the previous step (0.94 g, 1.02 mmol) in MeOH (36.80 mL) was slowly added an aqueous solution of LiOH (5.12 mL, 5.12 mmol). The reaction mixture was stirred at 0° C. for 2 h before the pH of the solution was adjusted to 5-6 by slow addition of 1 N HCl. The mixture was concentrated in vacuo and the crude residue was purified by reverse phase column chromatography to afford the title compound (0.46 g, 57% yield) as a white solid. (m/z): [M+H]$^+$ calcd for $C_{36}H_{46}H_8O_{12}$ 783.32 found 783.8. HPLC Method B Retention time 0.99 min.

Example C-1

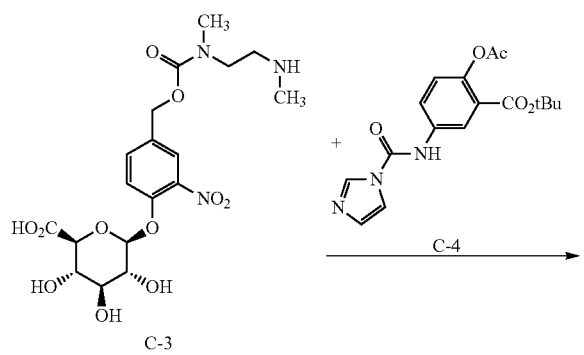

C-3

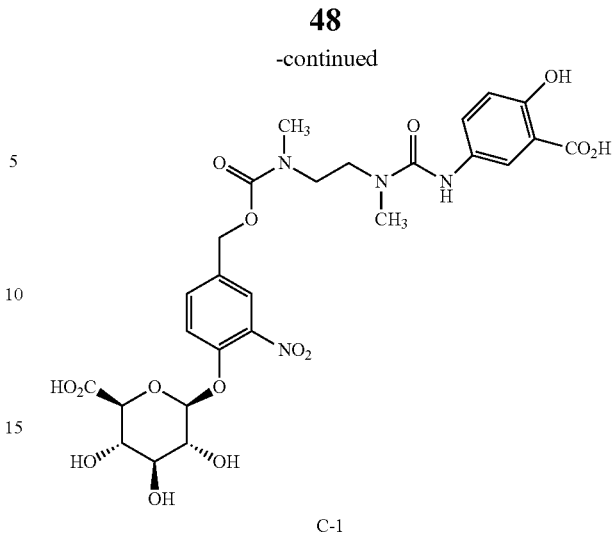

C-1

(a) Compound C-5

To a flask were added the TFA salt of compound C-3 (285 mg, 0.497 mmol) and Compound C-4 (445 mg, 1.289 mmol) followed by DMF (2.485 mL) and triethylamine (0.416 mL, 2.98 mmol). The next day the reaction mixture was concentrated by rotary evaporation and purified by normal phase column chromatography (0-15% MeOH in DCM over 15 min, then continuous 15% over 5 min) to provide the title compound (90 mg).

(b) Compound C-1

The product of the previous step (45 mg, 0.061 mmol) and potassium carbonate (33.8 mg, 0.244 mmol) were dissolved in MeOH (0.8 mL) and water (0.4 mL) and stirred at RT. After 2 h, MeOH was added to form an azeotrope with water, and DCM (0.4 mL) was added followed by TFA (0.4 mL, 5.19 mmol). The reaction mixture was concentrated by rotary evaporation, dissolved in 1:1 water:ACN, filtered, and purified by preparative HPLC to provide the title compound (17.7 mg, 97% purity) as an off-white powder. (m/z): [M+H]$^+$ calcd for $C_{26}H_{30}N_4O_{15}$ 639.17 found 639.2.

Preparation of Compound C-7

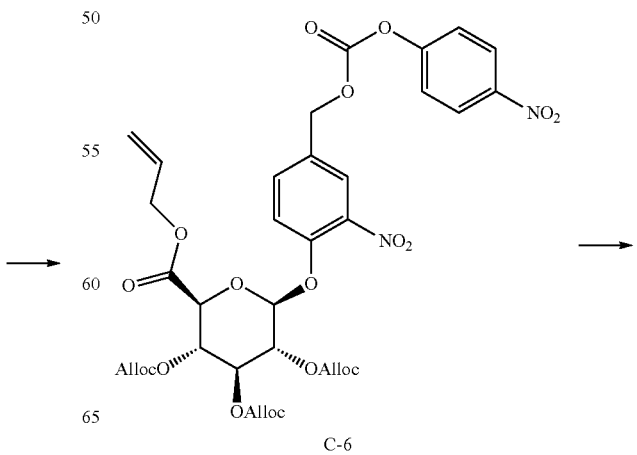

C-6

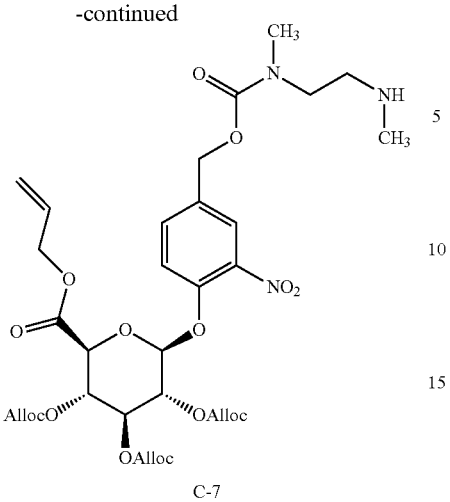

C-7

To a solution of compound C-6 (300 mg, 0.374 mmol) dissolved in DCM (3.74 mL) at 0° C. was added N,N-dimethylethylenediamine (159 µl, 1.495 mmol) in one portion. The reaction mixture was stirred at 0° C. for 30 min, diluted in DCM (15 mL) and washed with water (3×10 mL). The organic layer was washed with brine, separated, dried over sodium sulfate and filtered to provide the title intermediate as a yellow oil which was used without further purification. (m/z): [M+H]$^+$ calcd for $C_{33}H_{41}H_3O_{17}$ 752.24 found 752.4.

Preparation of Compound C-8

C-8

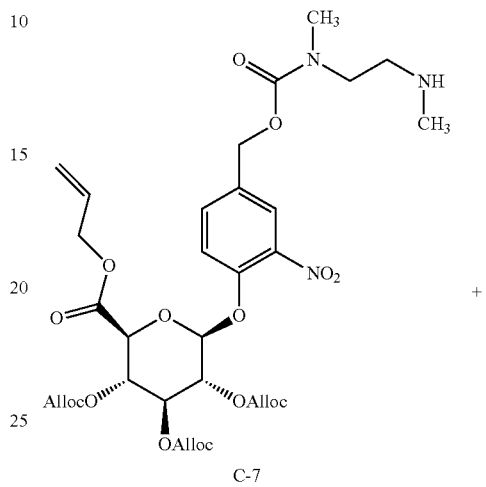

To a solution of sodium hydride (36.4 mg, 0.9105 mmol) dissolved in a mixture of THF (3.372 mL) and DMF (1.686 mL) was added bis(2,4-dinitrophenyl)carbonate (299 mg, 0.759 mmol). The reaction mixture was stirred at 0° C. for 1 h and then a solution of 2-(5-fluoro-4-methylpyridin-3-yl)-5-(4-methyl-6-(methylsulfonyl)pyridin-3-yl)-1H-indole (compound C-2M) (200 mg, 0.506 mmol) dissolved in THF (1.2 mL) was slowly added and the reaction mixture was warmed up to RT. After 9 h, saturated sodium bicarbonate was added and the reaction mixture was washed with brine. The organic layer was separated, dried over sodium sulfate, filtered and concentrated. The crude residue was purified by column chromatography (eluted with 0-80% EtOAc in hexanes) to provide the title intermediate (109 mg) as a brown colored oil. (m/z): [M+H]$^+$ calcd for $C_{28}H_{20}FN_5O_8S$, 606.10 found 606.3.

Example C-2

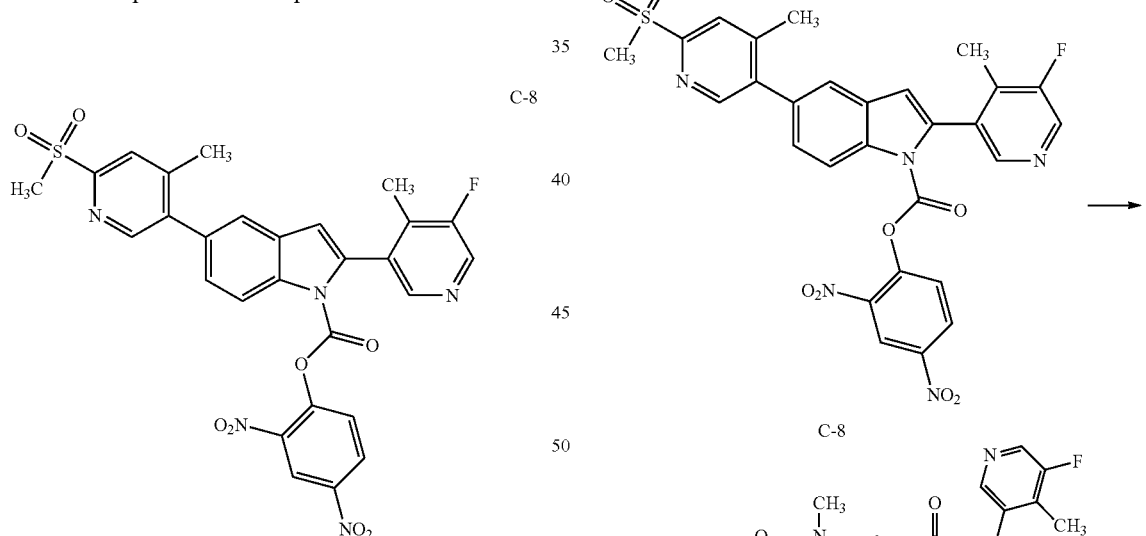

C-7

C-8

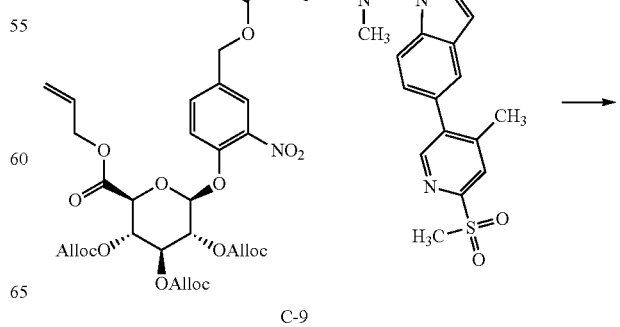

C-9

-continued

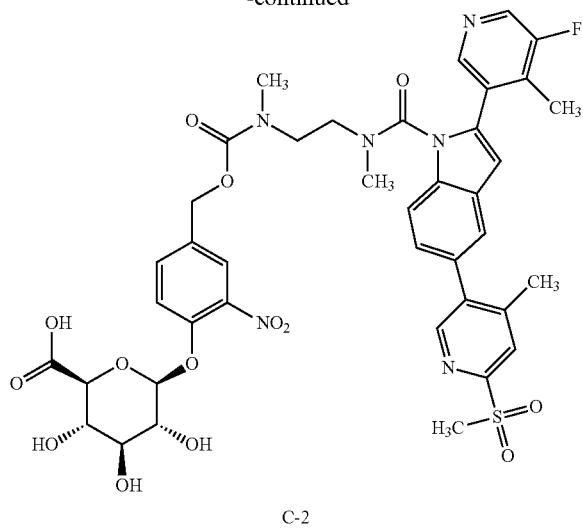

C-2

(a) Compound C-9

To a solution of compound C-8 (250 mg, 0.413 mmol) in DCM (4.13 mL) was added compound C-9 (310 mg, 0.413 mmol), followed by 4-dimethylaminopyridine (22 mg, 0.180 mmol). The reaction mixture was stirred at 40° C. for 1 h, cooled to RT and concentrated to provide the title intermediate which was used directly in the next step without purification. (m/z): [M+H]$^+$ calcd for $C_{55}H_{57}FN_6O_{20}S$, 1173.33 found 1173.4.

(b) Compound C-2

To a degassed solution of the product of the previous step (485 mg, 0.413 mmol) dissolved in THF (4.13 mL) was added tetrakis(triphenylphosphine)palladium(0) (47.7 mg, 0.041 mmol) and morpholine (360 µL 4.13 mmol). The reaction mixture was stirred at RT for 45 min and then water was added and the layers were separated. The organic layer was dried over sodium sulfate, filtered and concentrated under vacuum. The crude residue was purified by preparative HPLC and lyophilized to provide the title compound (136 mg, 99% purity) as a white powder. (m/z): [M+H]$^+$ calcd for $C_{40}H_{41}FN_6O_{14}S$, 881.24 found 881.2.

Biological Assays

The compounds of the invention have been characterized in one or more of the following biological assays. In the assay descriptions, the compound of formula 1 may alternatively be referenced as compound 1 and similarly for the additional compounds of the invention.

Assay 1: Biochemical JAK Kinase Assay

A panel of four LanthaScreen JAK biochemical assays (JAK1, 2, 3 and Tyk2) were carried in a common kinase reaction buffer (50 mM HEPES, pH 7.5, 0.01% Brij-35, 10 mM $MgCl_2$, and 1 mM EGTA). Recombinant GST-tagged JAK enzymes and a GFP-tagged STAT1 peptide substrate were obtained from Life Technologies.

Serially diluted compounds were pre-incubated with each of the four JAK enzymes and the substrate in white 384-well microplates (Corning) at ambient temperature for 1 h. ATP was subsequently added to initiate the kinase reactions in 10 µL total volume, with 1% DMSO. The final enzyme concentrations for JAK1, 2, 3 and Tyk2 are 4.2 nM, 0.1 nM, 1 nM, and 0.25 nM respectively; the corresponding Km ATP concentrations used are 25 µM, 3 µM, 1.6 µM, and 10 µM; while the substrate concentration is 200 nM for all four assays. The JAK1 kinase activity was also tested at 1 mM ATP concentration. Kinase reactions were allowed to proceed for 1 hour at ambient temperature before a 10 µL preparation of EDTA (10 mM final concentration) and Tb-anti-pSTAT1 (pTyr701) antibody (Life Technologies, 2 nM final concentration) in TR-FRET dilution buffer (Life Technologies) was added. The plates were allowed to incubate at ambient temperature for 1 h before being read on the EnVision reader (Perkin Elmer). Emission ratio signals (520 nm/495 nm) were recorded and utilized to calculate the percent inhibition values based on DMSO and background controls.

For dose-response analysis, percent inhibition data were plotted vs. compound concentrations, and $IC_{50}$ values were determined from a 4-parameter robust fit model with the Prism software (GraphPad Software). Results were expressed as $pIC_{50}$ (negative logarithm of IC50) and subsequently converted to $pK_i$ (negative logarithm of dissociation constant, Ki) using the Cheng-Prusoff equation. Table 1 summarizes results for compound 1 and tofacitinib (compound 2).

TABLE 1

| Enzymatic Potency | | |
| --- | --- | --- |
| Property | Compound 1 | Tofacitinib |
| JAK1 ($pK_i$) | <6.3 | 9.1 |
| JAK2 ($pK_i$) | <6.2 | 9.2 |
| JAK3 ($pK_i$) | <6.8 | 9.5 |
| TYK2 ($pK_i$) | <6 | 7.9 |
| JAK1 ($pIC_{50}$ at 1 mM ATP) | <5 | 7.7 |

Assay 2: Metabolic Stability of Compound 1 in β-Glucuronidase from *E. Coli*

To characterize the intermediate metabolites and final product of compound 1 in the presence of β-glucuronidase enzyme, compound 1 (30 µM in DMSO) was incubated at 37° C. in the presence of purified β-glucuronidase from *E. coli* (100 Units/mL in a 0.1 M potassium phosphate buffer) over a time course of 0-90 minutes. The incubations were quenched at timepoints 0, 1, 2, 3, 5, 10, 15, 30, 60, and 90 min by addition of 100 µL of ACN. Samples were diluted with water+1% formic acid (4×) and analyzed using a Thermo Q-Exactive™ LC-MS system. Compound 1 and tofacitinib concentrations were quantified by comparison with standard curves determined using the same dilutions as the samples.

Rapid disappearance of compound 1 (half-life<5 min) was accompanied with the rapid and transient formation of the aglycone intermediate (compound b in Scheme 2). The conversion of the aglycone intermediate to its subsequent diamine intermediate (compound d) and ultimate active metabolite (tofacitinib) was observed to be the slower rate-determining step. The concentration of tofacitinib was observed to increase gradually over the 90 min time course of the experiment to a final concentration of about 20 µM.

To demonstrate the observed conversion of compound 1 to tofacitinib is due to glucuronidase enzyme interaction, compound 1 (30 µM) was incubated with β-glucuronidase (45 Units/mL) and the known bacterial β-glucuronidase inhibitor amoxapine (100 µM). After a 60 min incubation, the final concentration of tofacitinib was 1 µM in the presence of the inhibitor as compared with 7 µM (no inhibitor).

Assay 3: Metabolic Stability in Homogenates Prepared from Rat Upper and Lower Intestinal Content The conversion of compound 1 to tofacitinib was evaluated in the intestinal lumen content prepared from the various GI segments isolated from freshly sacrificed rats. Each segment of content from the duodenum, jejunum, ileum, and colon was diluted 1:10 in Dulbecco's phosphate buffer saline (DPBS) solution. A 10 mM DMSO stock of compound 1 was diluted into DPBS to yield a final substrate concentration of 10 µM. The incubation was conducted in a water bath at 37° C. and time points were taken at 0, 5, 10, 20, 40 and 60 min. The total incubation volume was 400 µL and 40 µL aliquots were taken at each time point and diluted into 160 µL of 97% ACN+3% formic acid+an internal standard. The samples were centrifuged at 2200 rcf for 10 min and 50 µL of supernatant was diluted into 150 µL of water+1% formic acid. The samples were analyzed on an API 4000 mass spectrometer for compound 1 and tofacitinib. The half-life determined for the disappearance of compound 1 is summarized below.

gastrointestinal tract (sectioned approximately into thirds [U-1, U-2, U-3]). cecum, and lower gastrointestinal tract (sectioned approximately into halves [L-1, L-2]). Each tissue sample was rinsed with water, patted dry, transferred to a tared container, weighed, diluted with 3 times the weight of tissue by volume (w/v) with acidified water, homogenized at 6500 RPM (3×45 sec), and frozen. Concentrations of tofacitinib released from compound 1 and of $D_3$-tofacitinib in each tissue sample were determined as follows. The tissue samples were vortexed, combined with a 50 µL aliquot of rat plasma, extracted with 200 µL of ACN containing an internal standard and quantified against the internal standard by LC-MS. Concentrations of tofactinib released from compound 1 were measureable in plasma between 3 and 8 hours, in the stomach and sections U-1, U-2, and U-3 through 8 hours, and in the cecum, and sections L-1, and L-2 between 3 and 24 hours. Concentrations of $D_3$-tofacitinib were measureable in plasma between 0.5 and 8 hours, in the stomach and sections U-1, U-2, and U-3 through 8 hours, and in the cecum, and sections L-1, and L-2 between 3 and 24 hours. The resulting standard pharmacokinetic parameters, $C_{max}$ (maximum concentration) and AUC (0-t) (area under the curve of concentration vs. time, integrated to the last time point measured) are reported in Table 3.

TABLE 3

Tofacitinib and $D_3$-Tofacitinib Concentration Rat

| | Compound 1/Tofacitinib | | | $D_3$-Tofacitinib/$D_3$-Tofacitinib | | |
|---|---|---|---|---|---|---|
| Sample | $C_{max}$ (µg/mL) | AUC (0-t) (µg * hr/mL) | Tissue/Plasma Ratio | $C_{max}$ (µg/mL) | AUC (0-t) (µg * hr/mL) | Tissue/Plasma Ratio |
| Plasma | 0.009 | 0.044 | | 0.094 | 0.21 | |
| Stomach | 2.83 | 4.68 | 106 | 6.95 | 9.41 | 45 |
| U-1 | 3.51 | 6.39 | 145 | 5.40 | 7.01 | 33 |
| U-2 | 6.56 | 11.40 | 259 | 3.20 | 7.06 | 34 |
| U-3 | 10.40 | 37.90 | 859 | 3.39 | 11.20 | 53 |
| Cecum | 6.39 | 71.20 | 1615 | 0.85 | 10.10 | 48 |
| L-1 | 2.28 | 25.90 | 587 | 0.33 | 3.98 | 19 |
| L-2 | 2.41 | 23.70 | 537 | 0.31 | 3.33 | 16 |

TABLE 2

| Rat Intestinal Content | Compound 1 half-life |
|---|---|
| Duodenum | >60 min |
| Jejunum | >60 min |
| Ileum | 34 min |
| Colon | <5 min |

Assay 4: Oral Pharmacokinetics of Compound 1 in Rat

The objective of this study was to compare the gastrointestinal mucosal and plasma pharmacokinetics of compound 1 and tofacitinib following a simultaneous oral dose. Male Sprague Dawley rats (n=3/time point) were dosed via oral gavage with 3 mg/kg of compound 1 and a dose normalized 1.2 mg of trideuterium labeled tofacitinib ($D_3$-tofacitinib) formulated as a solution in 5% DMSO+1% hydroxypropyl methyl cellulos in water. At each time point (0.5, 1, 3, 6, 8 and 24 h), plasma samples were taken by cardiac puncture and the following tissues were collected: stomach, upper

Assay 5: Oral Pharmacokinetics of Compound 1 in Cynomolgus Monkey

The objective of this study was to compare the colonic and plasma pharmacokinetics of compound 1 and tofacitinib following a simultaneous oral dose. Male cynomolgus monkeys (n=1/time point) were dosed via oral gavage with 3 mg/kg of compound 1 and 2.1 mg/kg of trideuterium labeled tofacitinib ($D_3$-tofacitinib) formulated as a solution in 98.5% pH 6 citrate buffer+1% hydroxypropyl methylcellulose+ 0.5% Tween 20. At each time point (0.5, 1, 3, 6, 9 and 24 h), plasma samples were taken from the femoral vein and the following tissues were collected: stomach, upper gastrointestinal tract (sectioned approximately into thirds [U-1, U-2, U-3]). cecum, proximal colon, distal colon, and rectum. Each tissue sample was rinsed with water, patted dry, transferred to a tared container, weighed, flash frozen, pulverized, and stored at −70° C. An approximately 2 g aliquot was diluted 3 times the weight of tissue by volume (w/v) with control rat plasma in water, homogenzied, and stored at −70° C. Concentrations of tofacitinib released from compound 1 and of $D_3$-tofacitinib in each tissue sample were determined as follows. The samples were vortexed, and a 50 μL aliquot of plasma or prepared tissue sample was extracted with 200 μL of ACN containing an internal standard and quantified against the internal standard by LC-MS. Concentrations of tofactinib released from compound 1 were measureable in plasma and all tissue samples between 0.5 and 24 hours. Concentrations of $D_3$-tofacitinib were measureable in plasma and stomach between 0.5 and 9 hours, and in all other tissue sections between 0.5 and 24 hours. The resulting standard pharmacokinetic parameters, $C_{max}$ (maximum concentration) and AUC (0-t) (area under the curve of concentration vs. time, integrated to the last time point measured) are reported in Table 4.

TABLE 4

Tofacitinib and $D_3$-Tofacitinib Concentration Monkey

| | Compound Administered/Analyte | | | | | |
|---|---|---|---|---|---|---|
| | Compound 1/Tofacitinib | | | $D_3$-Tofacitinib/$D_3$-Tofacitinib | | |
| Sample | $C_{max}$ (μg/mL) | AUC (0-t) (μg * hr/mL) | Tissue/Plasma Ratio | $C_{max}$ (μg/mL) | AUC (0-t) (μg * hr/mL) | Tissue/Plasma Ratio |
| Plasma | 0.14 | 0.78 | | 0.35 | 0.83 | |
| Stomach | 8.01 | 10.5 | 13.4 | 17.9 | 17.1 | 20.7 |
| U-1 | 19.6 | 21.5 | 27.5 | 18.5 | 15.7 | 19.0 |
| U-2 | 28.8 | 40.6 | 51.9 | 7.96 | 11.1 | 13.4 |
| U-3 | 21.7 | 55.7 | 71.1 | 8.96 | 16.4 | 19.9 |
| Cecum | 31.7 | 152 | 194 | 4.75 | 22.8 | 27.6 |
| Proximal colon | 19.5 | 117 | 149 | 3.63 | 15.9 | 19.2 |
| Distal colon | 14.4 | 46.7 | 59.6 | 3.30 | 8.86 | 10.7 |
| Rectum | 1.99 | 26.3 | 33.6 | 1.00 | 7.63 | 9.24 |

Assay 6: Mouse Model of Oxazolone-Induced Colitis

Oxazolone-induced colitis is an experimental model that has a histological resemblance to human ulcerative colitis (Heller et al. *Immunology*, 2002, 17, 629-638). Adult BALB/C mice (25-28 g, 9-12 weeks of age) from BioNeeds (India) were used in the assay. On day 1, animals were lightly anesthetized with isoflurane and the hairs between the shoulder were carefully removed before oxazolone (6 mg/mouse, 100 μL 4:1 acetone: olive oil formulation) or vehicle solution was slowly applied for skin sensitization. Six days after skin sensitization, the mice were fasted overnight, anesthetized with ketamine and xylazine administered IP, and a 1 mL syringe filled with oxazolone solution, was inserted carefully ~3.8 cm into the colon of the mouse. Animals were kept in a head down position and oxazolone (0.5 mg/50 μL/mouse in 50% ethanol) or 50% ethanol/saline was rectally instilled very slowly over a minute. The mice were held vertically (head down) for another minute to ensure that the entire oxazolone solution remained inside the colon. Drug treatment (PO, BID or TID) or vehicle was initiated the evening prior to the oxazolone intrarectal (IR) challenge. On both first (Day 1) and second (Day 2) days post-oxazolone IR challenge, the Disease Activity Index (DAI) was assessed by treatment-blinded experimenters for each mouse, according to the following subscores: stool consistency (0, normal; 2, loose; 4, diarrhea), gross bleeding and hemocult test (0, absence; 2, blood tinged; 4, overt blood presence), and weight loss (0, none; 1, 1%-5%; 2, 6%-10%; 3, 11%-15%; 4, more than 15%); DAI=average of (stool consistency+blood presence+weight loss scores).

An area-under-the-curve (AUC) calculation based on total DAI scores was performed to track disease progression during the course of the experiment. AUC for each experimental group was calculated as: AUC=[(Day 1−Day 0)*Average (DAI Score of Day 0 & Day 1)]+[(Day 2−Day 1)*Average (DAI Score of Day 1 & Day 2)]. A Student's t-test compared the DAI AUC score of the vehicle/vehicle and vehicle/oxazolone groups to evaluate whether disease was induced following oxazolone treatment. This was followed by a one way ANOVA, with Dunnett's post hoc test, to compare the DAI AUC score of the vehicle/oxazolone and test compound/oxazolone groups. Statistical significance was defined by an a level set at $p<0.05$.

In the oxazolone-induced acute colitis model, the compound of formula 1 (3, 10, 30 and 60 mg/kg, PO, BID) produced a significant reversal of oxazolone-induce colitis, of similar magnitude to that achieved by tofacitinib (30 and 60 mg/kg, PO, BID). In a separate experiment in the oxazolone model, the compound of formula 4 (3, 10, and 30 mg/kg, PO, BID) produced a significant reversal of oxazolone-induce colitis, of similar magnitude to that achieved by tofacitinib (30 mg/kg, PO, BID)

Assay 7: Immunosuppression Effects in Mouse Splenic Natural Killer (NK) Cells

Depletion of mouse splenic cells is an experimental model of immunosuppression (Kudlacz et al., *Am. J. of Transplantation*, 2004, 4, 51-57). Compound 1 was assessed in the mouse splenic cell model following the same treatment paradigm as that used in the oxazolone-induced colitis model (Assay 6).

Adult male Balb/C mice (12-14 weeks of age) from Harlan were used for the study. Compound 1 (1, 3 and 10 mg/kg, BID) and tofacitinib (10, 30, and 60 mg/kg, BID) were dosed orally for three days to naïve mice. Spleens were harvested 30 min or 3 h post last dose and crushed immediately for cell subtype staining. Prior to fixation, fluorophore-labelled antibodies for CD19 (FITC; B cells), CD3e (PE; pan T cells) and DX5 (APC; NK cells) were incubated with splenocyte samples from each animal to allow for simultaneous, multiple subtype % analysis on the flow cytometer. The number of total spleen cells for each animal was measured by Scepter™ 2.0 Handheld Automated Cell Counter.

The absolute number of lymphocyte subtype population (e.g., splenic B, T and NK cells) was calculated from the percentage of each subtype times total spleen cells for each animal. A one way ANOVA, with Dunnett's post hoc test, was used to compare the splenic lymphocytes number of the vehicle and test compound groups. The α level was set at p<0.05. Data were presented as the mean±SEM for each group.

Tofacitinib (10, 30 and 60 mg/kg; PO, TID) dose-dependently and significantly decreased splenic NK cell counts. In the same study, splenic NK cell counts were unaffected by compound 1 at PO (BID) doses up to 10 mg/kg (the maximum dose tested). No treatment effect was observed for the B and T cell populations with either compound.

This data, in conjunction with the anti-colitic effect of compound 1 in the mouse model of oxazolone-induced colitis (Assay 6), allow a functional therapeutic index to be computed as reported below in Table 5

TABLE 5

Functional Therapeutic Index

| Compound | In vivo efficacy (oxazolone colitis)* (mg/kg) | Systemic functional activity (splenic NK depletion) (mg/kg) | Functional therapeutic index (fold) |
|---|---|---|---|
| Compound 1 | 3 | >10 | >3 |
| Tofacitinib | 30 | 10 | 0.3 |

*Effective dose that exhibits a comparable pharmacological effect in the oxazolone model compared to its vehicle Assay 8: Rat Colon Fecal Homogenate Stability The objective of this study was to determine the stability of the present compounds in rat colon fecal homogenate, i.e. the half-life for decomposition in the presence of the β-glucuronidase in rat colon feces.

Following sacrifice of a naïve male rat (~300 g) by cardiac puncture exsanguination, the colon was ligated and removed to an anaerobic chamber (AS-580, Anaerobe Systems). The fecal content was removed within the chamber and was diluted 1:10 (1 gram to 9 mL phosphate buffer) and then homogenized using a handheld Omni Tissue Master. The fecal homogenate was centrifuged at 2000 g for 10 min to remove bulk and the supernatant was removed and used for the incubations.

Test articles and a positive control (sulfasalazine) were prepared as 10 mM DMSO stocks. The final substrate concentration of each assay was 10 μM (30 μM for compound 5). Reactions were started by adding a 5 μL aliquot of diluted test compound stock into 300 μL of rat fecal supernatant-homogenate. At 0, 15, 30, 60, 90, and 120 min post reaction initiation, a 50 μL aliquot was removed into 200 μL of acetonitrile with 3% formic acid and an internal standard molecule. All samples were centrifuged at 2000 g for 10 min after which 50 μL of supernatant was diluted into 150 μL of water for analysis on an LC-MS system. In vitro half-lives for loss of pro-drug were calculated as follows: (T½=0.693/elimination rate constant).

TABLE 6

In vitro colonic stability

| Compound No. | T½ (min) |
|---|---|
| 1 | 1-15 (Multiple values) |

TABLE 6-continued

In vitro colonic stability

| Compound No. | T½ (min) |
|---|---|
| 4 | 1-13 (Multiple values) |
| 5 | 6 |
| 6 | 7 |
| 7 | 3-8 (Multiple values) |

Assay 9: Oral Pharmacokinetics in Mouse

The object of this study was to assess the plasma and colon conversion of prodrugs of the invention to tofacitinib following oral dosing in mice.

Male Balb/c mice (n=2/timepoint) received a single PO oral gavage dose (5 mg/kg in 1:20 mixture of 5% DMSO and 1% HPMC) of test compounds. At 2 hr and 6 hr post dosing mice were sacrificed via cardiac puncture exsanguination, resulting blood samples were placed into Microtainer® tubes containing NaF and then placed on ice. Plasma was obtained by centrifugation (eppendorf centrifuge, 5804R) for 4 min at approximately 12,000 rpm at 4° C.

The colons were removed from exsanguinated mice and the colon fecal contents gently removed. The colons were flushed with saline and patted dry. They were then homogenized in 3x volume of sterile water using a Precellys homogenizer at approximately 4° C. All samples were stored at −80° C. for later bioanalysis.

Concentrations of tofacitinib released from prodrug in each tissue sample were determined as follows: The plasma and colon homogenate samples were vortexed, combined with a 50 μL aliquot of rat plasma, extracted with 200 μL of ACN containing an internal standard and quantified against the internal standard by LC-MS. An area under the concentration curve ($AUC_{0-6\ hr}$) was calculated for plasma and colon test compound and liberated tofacitinib. The key parameter to assess suitability was tofacitinib colon/plasma AUC ratio.

TABLE 7

Tofacitinib Concentration Mouse

| Compound No. | Plasma AUC (μg * hr/mL) | Colon AUC (μg * hr/g) | Colon/Plasma Ratio |
|---|---|---|---|
| 1 | 0.013 | 7.6 | 585 |
| 3 | 0.001 | 9.03 | 9030 |

Assay 10: Oral Pharmacokinetics in Rat

The object of this study was to assess the plasma and colon conversion of prodrugs of the invention to tofacitinib following oral dosing in rats.

Male Sprague Dawley rats (n=2/timepoint) received a single PO oral gavage dose (5 mg/kg in 1:20 mixture of 5% DMSO and 1% HPMC) of test compounds. At 0.5, 1, 3, 6 and 24 hr post dosing rats were sacrificed via cardiac puncture exsanguination, resulting blood samples were placed into Microtainer® tubes containing NaF and then placed on ice. Plasma was obtained by centrifugation (Eppendorf centrifuge, 5804R) for 4 minutes at approximately 12,000 rpm at 4° C.

The colons were removed from exsanguinated rats and the colon contents gently removed. The colons were flushed with saline and patted dry. They were then homogenized in 3× the weight of sterile water using a Precellys homogenizer at approximately 4° C. All samples were stored at −80° C. for later bioanalysis.

Concentrations of tofacitinib released from prodrug in each tissue sample were determined as follows: The plasma and colon samples were vortexed, combined with a 50 μL aliquot of rat plasma, extracted with 200 μL of ACN containing an internal standard and quantified against the internal standard by LC-MS. An area under the concentration curve ($AUC_{0-6\ hr}$) was calculated for plasma and colon test compound and liberated tofacitinib. The key parameter to assess suitability was tofacitinib colon/plasma AUC ratio.

TABLE 8

| | Tofacitinib Concentration Rat | | |
|---|---|---|---|
| Compound No. | Plasma AUC (μg * hr/mL) | Colon AUC (μg * hr/g) | Colon/Plasma Ratio |
| 1 | 0.11 | 14.3 | 130 |
| 3 | 0.09 | 35.9 | 399 |
| 4 | 0.03 | 11.8 | 393 |
| 7 | 0.06 | 10.8 | 171 |

Assay 11: Metabolic Stability of Comparison Compounds in Rat Colon Content

Colonic fecal content was harvested from a naïve male Sprague Dawley rat and was diluted 1:10 (1 gram to 9 mL phosphate buffer) and then homogenized using a handheld Omni Tissue Master. Test compounds, comparison compounds C-1 and C-2 as well as the compound of the invention, compound 1, were prepared as 10 mM DMSO stock solutions and diluted into phosphate buffer to a final substrate concentration of 10 μM. A 5 μL aliquot of diluted test compound was spiked into 300 4 of rat colonic content homogenate to begin the reaction at 37° C. Aliquots (50 μL) were removed from the incubation at the following time points (0, 15, 50, 85, and 120 min) and added into 200 μL of ACN with 3% formic acid and an internal standard molecule. Standard curves of each metabolite, tofacitinib, 5-ASA (compound C-1M), and the CRAC inhibitor (compound C-2M), were prepared using the same matrix and dilution procedure as the samples. All samples were centrifuged at 2000×g for 10 min after which 50 μL of supernatant was diluted into 150 4 of water and analyzed using a Thermo Q-Exactive LC-MS system. GraphPad Prism and Microsoft Excel were used to tabulate and plot the data.

Following incubation at a substrate concentration of 10 μM in rat colonic content the comparison compounds as well as the compound of the invention all demonstrated rapid loss of parent molecule in the incubation (half-lives<15 min). However, upon measurement of the active metabolite of each pro-drug, only compound 1 generated measurable levels of its active metabolite, tofacitinib. A tofacitinib concentration of 8.8 μM was measured after 120 min incubation.

In contrast, compounds C-1 and C-2 failed to generate any measurable amounts of their active metabolites (compound C-1M and C-2M, respectively). The time course of metabolite production over 120 min is illustrated in FIG. 1.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

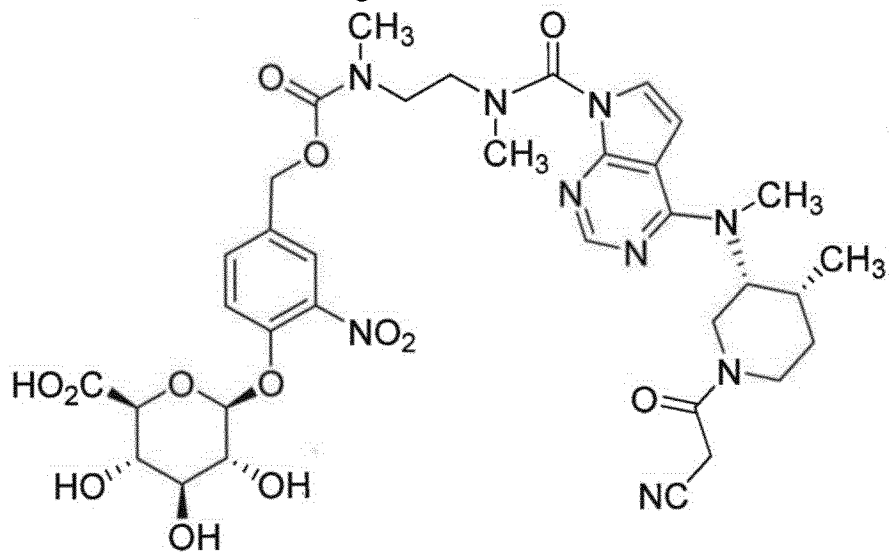

What is claimed is:

1. A compound of formula (I):

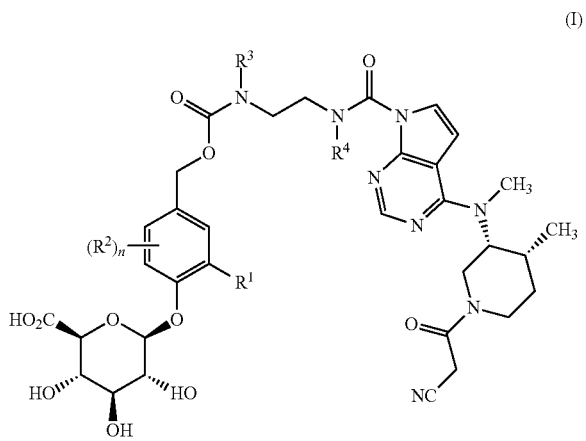

wherein
n is 0, 1 or 2;
$R^1$ is selected from hydrogen, $C_{1-4}$ alkyl, $C_{1-3}$ alkoxy, amino, nitro, halo, cyano, hydroxy, and trifluromethyl;
each $R^2$, when present, is independently selected from $C_{1-4}$ alkyl, $C_{1-3}$ alkoxy, amino, nitro, halo, cyano, hydroxyl, and trifluromethyl;
$R^3$ is hydrogen, methyl or ethyl;
$R^4$ is hydrogen, methyl or ethyl;
or a pharmaceutically-acceptable salt thereof.

2. The compound of claim 1, or a pharmaceutically-acceptable salt thereof, wherein $R^1$ is hydrogen.

3. The compound of claim 1, or a pharmaceutically-acceptable salt thereof, wherein $R^1$ is nitro.

4. The compound of claim 1, or a pharmaceutically-acceptable salt thereof, wherein $R^1$ is amino.

5. The compound of claim 1, or a pharmaceutically-acceptable salt thereof, wherein n is 0.

6. The compound of claim 1, or a pharmaceutically-acceptable salt thereof, wherein n is 1.

7. A compound of formula (II):

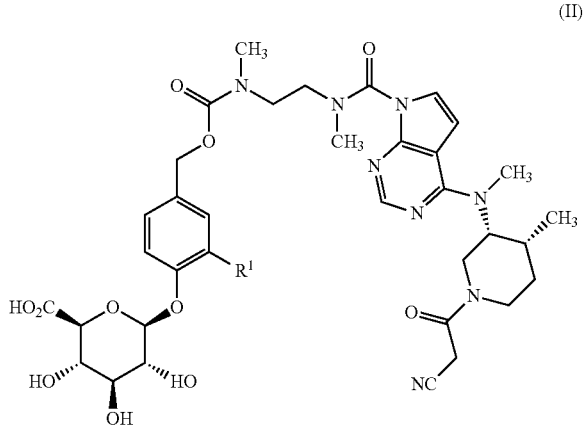

wherein

R¹ is selected from hydrogen, $C_{1-4}$ alkyl, $C_{1-3}$ alkoxy, amino, nitro, halo, cyano, hydroxy, and trifluromethyl;

or a pharmaceutically-acceptable salt thereof.

8. The compound of claim 7, or a pharmaceutically-acceptable salt thereof, wherein R¹ is selected from hydrogen, methyl, methoxy, amino, nitro, and chloro.

9. The compound of claim 7, or a pharmaceutically-acceptable salt thereof, wherein R¹ is hydrogen.

10. The compound of claim 7, or a pharmaceutically-acceptable salt thereof, wherein R¹ is amino.

11. A compound of formula 1:

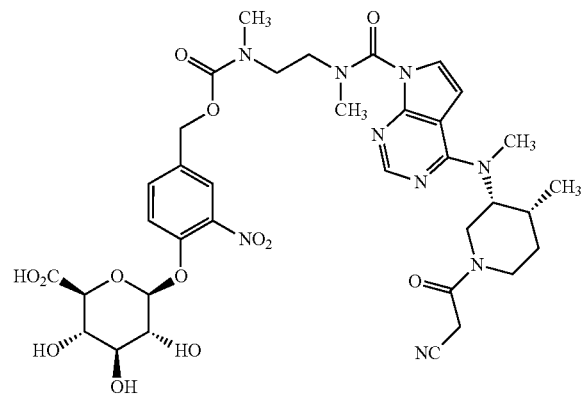 [SMILES: C[C@@H]1CCN(C(=O)CC#N)C[C@@H]1N(C)c1ncnc2c1ccn2C(=O)N(C)CCN(C)C(=O)OCc1ccc(O[C@@H]2O[C@H](C(=O)O)[C@@H](O)[C@H](O)[C@H]2O)c([N+](=O)[O-])c1]

1 or a pharmaceutically acceptable salt thereof.

12. The compound of claim 11, wherein the compound is

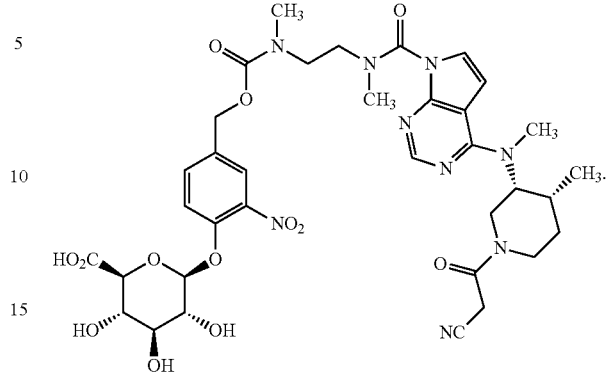

13. The compound of claim 11, wherein upon contact with a β-glucuronidase enzyme, a compound of formula 2:

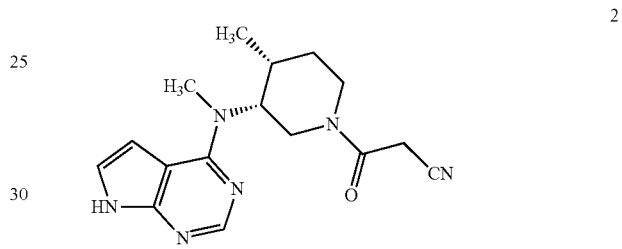

2 or a salt thereof is produced.

14. A pharmaceutical composition comprising a pharmaceutically acceptable-carrier and a compound of any one of claims 1, 7, and 11 to 12.

* * * * *

UNITED STATES PATENT AND TRADEMARK OFFICE
CERTIFICATE OF CORRECTION

Page 1 of 2

PATENT NO. : 10,435,428 B2
APPLICATION NO. : 15/358462
DATED : October 8, 2019
INVENTOR(S) : Ryan Hudson et al.

It is certified that error appears in the above-identified patent and that said Letters Patent is hereby corrected as shown below:

In the Claims

At Column 60, Lines 11-26, the figure should be:

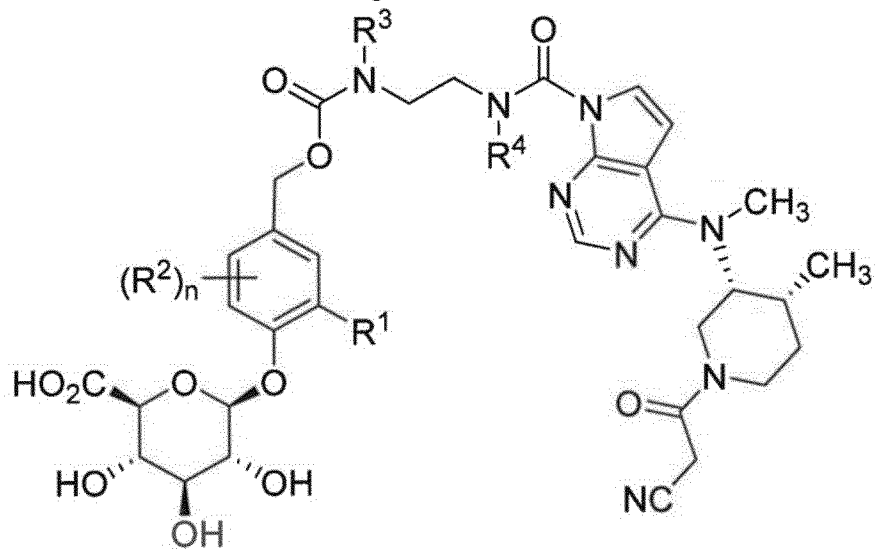

Signed and Sealed this
Seventeenth Day of March, 2020

Andrei Iancu
*Director of the United States Patent and Trademark Office*

CERTIFICATE OF CORRECTION (continued)
U.S. Pat. No. 10,435,428 B2

At Column 60, Lines 50-66, the figure should be:

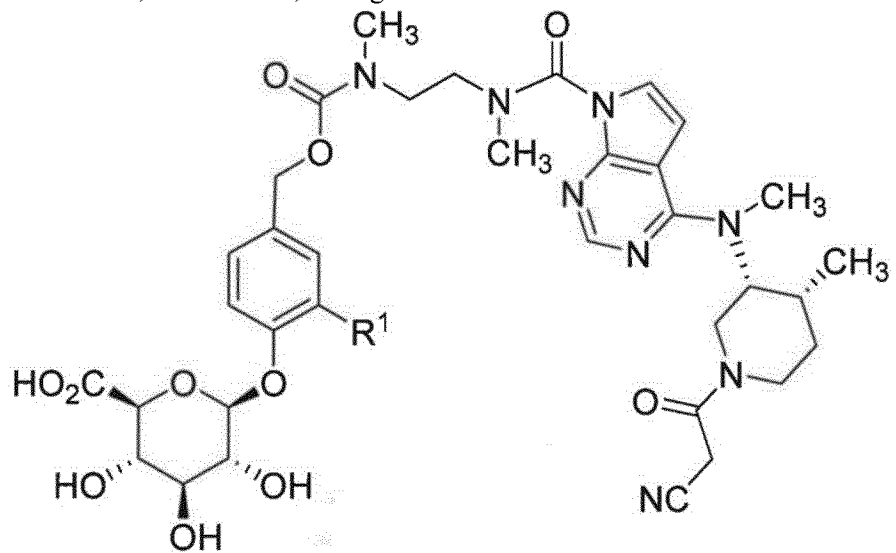

At Column 61, Lines 21-35, the figure should be: